United States Patent
Bootsma et al.

(10) Patent No.: US 10,837,029 B2
(45) Date of Patent: *Nov. 17, 2020

(54) METHODS AND SYSTEMS FOR GRINDING CORN AND MAKING ETHANOL THEREFROM

(71) Applicant: FLINT HILLS RESOURCES, LP, Wichita, KS (US)

(72) Inventors: Jason Bootsma, Wichita, KS (US); James Richard Reynolds, Muscatine, IA (US)

(73) Assignee: Flint Hills Resources, LP, Wichita, KS (US)

( * ) Notice: Subject to any disclaimer, the term of this patent is extended or adjusted under 35 U.S.C. 154(b) by 201 days.

This patent is subject to a terminal disclaimer.

(21) Appl. No.: 15/529,014

(22) PCT Filed: Nov. 23, 2016

(86) PCT No.: PCT/US2016/063657
§ 371 (c)(1),
(2) Date: May 23, 2017

(87) PCT Pub. No.: WO2017/091760
PCT Pub. Date: Jun. 1, 2017

(65) Prior Publication Data
US 2017/0268024 A1 Sep. 21, 2017

Related U.S. Application Data

(60) Provisional application No. 62/260,181, filed on Nov. 25, 2015.

(51) Int. Cl.
| | |
|---|---|
| *C12P 7/10* | (2006.01) |
| *C12M 1/33* | (2006.01) |
| *C12P 19/04* | (2006.01) |
| *C12M 1/00* | (2006.01) |
| *C12P 7/14* | (2006.01) |
| *C12P 7/06* | (2006.01) |
| *B02C 9/00* | (2006.01) |
| *C11B 1/02* | (2006.01) |
| *C11B 1/10* | (2006.01) |
| *C12P 19/16* | (2006.01) |
| *B02C 23/08* | (2006.01) |

(52) U.S. Cl.
CPC .................... *C12P 7/10* (2013.01); *B02C 9/00* (2013.01); *C11B 1/02* (2013.01); *C11B 1/10* (2013.01); *C12M 45/02* (2013.01); *C12M 45/04* (2013.01); *C12M 45/09* (2013.01); *C12P 7/06* (2013.01); *C12P 7/14* (2013.01); *C12P 19/04* (2013.01); *C12P 19/16* (2013.01); *C12Y 302/01001* (2013.01); *B02C 23/08* (2013.01); *C12P 2201/00* (2013.01); *C12P 2203/00* (2013.01); *Y02E 50/16* (2013.01); *Y02E 50/17* (2013.01)

(58) Field of Classification Search
None
See application file for complete search history.

(56) References Cited

U.S. PATENT DOCUMENTS

| | | | |
|---|---|---|---|
| 2,478,937 A | 8/1949 | Niethamer | |
| 3,538,551 A | 11/1970 | Joa | |
| 3,761,027 A | 9/1973 | Mendoza | |
| 4,056,636 A | 11/1977 | Muller | |
| 4,565,330 A | 1/1986 | Katoh | |
| 5,195,684 A * | 3/1993 | Radzins | D21B 1/066 |
| | | | 241/152.2 |
| 6,117,321 A | 9/2000 | Johnston | |
| 6,230,995 B1 | 5/2001 | Niemi et al. | |
| 6,509,180 B1 | 1/2003 | Verser et al. | |
| 7,083,954 B2 | 8/2006 | Jakel et al. | |
| 7,384,010 B2 | 6/2008 | Horigane et al. | |
| 7,507,562 B2 | 3/2009 | Verser et al. | |
| 7,699,255 B2 | 4/2010 | Kapper | |
| 7,842,484 B2 | 11/2010 | Lewis | |
| 7,857,608 B2 | 12/2010 | Fabbricante et al. | |
| 7,886,996 B2 | 2/2011 | Horigane et al. | |
| 7,888,082 B2 | 2/2011 | Verser et al. | |

(Continued)

FOREIGN PATENT DOCUMENTS

WO 2017/091766 A1 6/2017

OTHER PUBLICATIONS

Akinoso et al. "Work Index and Milling Efficiency of Size Reduction of Maize Using Plate Mill.", Agricultural Engineering Today., vol. 36, 2012, pp. 22-28 (Year: 2012).*
Pleasant Hill Grain, website catalog pp. 1-8, ABC Hansen Disc Mill, Aug. 9, 2015.
Particle Size Distributions of Ground Corn and DDGS from Dry Grind Processing, Rausch et al., Transactions of the ASAE, vol. 48(1), pp. 273-277, 2005.
Disc Mill DM 400-Retsch, Powerful grinding and robust design, Aug. 19, 2015.
Ethanol Producers Talk Shop, pp. 1-3, Ron Kotrba, Aug. 1, 2006.
Fluid Quip-Ethanol Industry, Corn Wet Milling Process Description, website pp. 1-6, Aug. 19, 2015.

(Continued)

*Primary Examiner* — Christian L Fronda

(57) ABSTRACT

Processes for grinding corn, ground corn products, and processes for making ethanol from the ground corn products. In some examples, a process for making ethanol can include introducing a plurality of corn pieces into a mill. The process can also include milling the corn pieces in the mill to produce a ground corn product. Greater than 25 wt % of the ground corn product can have a particle size of greater than 105 μm, as measured according to AOAC 965.22-1966. Greater than 80 wt % of the ground corn product can have a particle size of 425 μm or less, as measured according to AOAC 965.22-1966. The process can also include processing the ground corn product to produce a fermentation mash that can include ethanol and separating at least a portion of the ethanol from the fermentation mash to produce a stillage.

13 Claims, 6 Drawing Sheets

(56) References Cited

U.S. PATENT DOCUMENTS

| | | | |
|---|---|---|---|
| 7,954,734 | B2 | 6/2011 | Hata |
| 8,236,086 | B2 | 8/2012 | Janssen |
| 8,449,728 | B2 | 5/2013 | Redford |
| 8,454,802 | B2 | 6/2013 | Redford |
| 8,563,282 | B2 | 10/2013 | Galvez, III et al. |
| 8,597,917 | B2 | 12/2013 | Medoff et al. |
| 8,603,786 | B2 | 12/2013 | Redford |
| 8,778,433 | B2 | 7/2014 | Lee |
| 8,813,973 | B2 | 8/2014 | Lee |
| 9,012,191 | B2 | 4/2015 | Lee |
| 9,114,114 | B2 * | 8/2015 | Anderson ............... A23G 1/32 |
| 10,059,966 | B2 * | 8/2018 | Bootsma ................... C12P 7/10 |
| 2007/0031953 | A1 | 2/2007 | Dunson, Jr. et al. |
| 2007/0148318 | A1 | 6/2007 | Rubio et al. |
| 2007/0190626 | A1 | 8/2007 | Wilkening et al. |
| 2009/0093027 | A1 | 4/2009 | Balan et al. |
| 2010/0055741 | A1 | 3/2010 | Galvez, III et al. |
| 2011/0003341 | A1 | 1/2011 | Nojiri et al. |
| 2011/0142788 | A1 | 6/2011 | Sellier |
| 2012/0064213 | A1 | 3/2012 | Lee |
| 2012/0244590 | A1 | 9/2012 | Lee |
| 2013/0165678 | A1 | 6/2013 | Kohl et al. |
| 2014/0024084 | A1 | 1/2014 | Galvez, III et al. |
| 2014/0110512 | A1 | 4/2014 | Lee |
| 2014/0155639 | A1 * | 6/2014 | Sticklen ................. C11B 13/00 554/13 |
| 2014/0178946 | A1 | 6/2014 | Galvez, III et al. |
| 2014/0242251 | A1 | 8/2014 | Bootsma |
| 2014/0315259 | A1 | 10/2014 | Woods |
| 2015/0056327 | A1 | 2/2015 | Redford |
| 2015/0118727 | A1 | 4/2015 | Escudero et al. |
| 2015/0147786 | A1 | 5/2015 | Clarkson et al. |
| 2015/0152196 | A1 * | 6/2015 | Phanopoulos .......... C08B 37/00 536/56 |
| 2015/0181911 | A1 | 7/2015 | Redford |
| 2015/0181912 | A1 | 7/2015 | Redford |
| 2017/0253892 | A1 | 9/2017 | Bootsma |

OTHER PUBLICATIONS

International Standard, ISO13320, Particle size analysis-Laser diffraction methods, pp. 1-58.
PCT/US2016/063657 International Search Report and Written Opinion, dated Feb. 7, 2017.
PCT/US2016/063666 International Search Report and Written Opinion, dated Mar. 27, 2017.
A Lecture on Pressure Screening, James A. Olson, Mechanical Engineering Department, University of British Columbia, Aug. 21, 2003.
International Search Report and Written Opinion received for PCT application No. PCT/US2017/034324, dated Aug. 14, 2017, 8 pages.
Nouroddini et al., "Stagewise Dilute-Acid Pretreatment and Enzyme Hydrolysis of Distillers' Grains and Corn Fiber", Appl Biochem Biotech, 159, pp. 553-567, 2009.
Sluiter, A., et al., "Determination of Total Solids in Biomass and Total Dissolved Solids in Liquid Process Samples", National Renewable Energy Laboratory, pp. 1-9, 2008.
Sluiter, A., et al., "Determination of Ash in Biomass", National Renewable Energy Laboratory, pp. 1-8, 2005.
Hames, B., et al., "Determination of Protein Content in Biomass", National Renewable Energy Laboratory, pp. 1-8, 2008.
Sluiter, A., et al., "Determination of Extractives in Biomass", National Renewable Energy Laboratory, pp. 1-12, 2005.
Sluiter, A., et al., "Determination of Structural Carbohydrates and Lignin in Biomass", National Renewable Energy Laboratory, pp. 1-18, 2012.
Sluiter, A., et al., "Determination of starch in solid biomass samples", National Renewable Energy Laboratory, pp. 1-7, 2005.
Ankom, "Acid Detergent Fiber in Feeds-Filter Bag Technique (for A2000 and A2000I)", ADF method, pp. 1-2, 2017.
Cheetham, et al., "Variation in crystalline type with amylose content in maize starch granules: an X-ray powder diffraction study", Carbohydrate Polymers, vol. 36, pp. 277-284, 1998.
Nara, S., et al., "Studies on the Relationship Between Water-satured State and Crystallinity by the Diffraction Method for Moistened Potato Starch", starch, vol. 35, Issue 12, pp. 407-410, 1983.
Benedetti, A. et al., "X-ray diffraction methods to determine crystallinity and preferred orientation of lithium disilicate in Li-Zn-silicate glass-ceramic fibres", Journal of Materials Science, vol. 18, pp. 1039-1048, 1983.
AOAC International "Aoac 965.22-1966", pp. 1, 1996.
Wongsagonsup et al., "Effects of different mill types on ethanol production using uncooked dry-grind fermentation and characteristics of residual starch in distiller's dried grains (DDG)", Cereal Chemistry, vol. 94, Feb. 27, 2017, pp. 645-653.
Chatzifragkou et al., "Biorefinery strategies for upgrading distillers' driedgrains with solubles (DDGS)", Process Biochemistry, vol. 50, 2015, pp. 2194-2207.
Kim et al., "Process simulation of modified dry grind ethanol plant with recycle of pretreated and enzymatically hydrolyzed distillers' grains", Bioresource Technology, vol. 99, 2008, pp. 5177-5192.
Rosentrater, "Production and use of evolving corn-based fuel ethanol coproducts in the U.S." In: Biernat (Editor): 11 Biofuels—Status and perspective, 2015, pp. 81-98.
PCT/IB2018/053688, International Search Report and Written Opinion, Aug. 21, 2018.

* cited by examiner

METHODS AND SYSTEMS FOR GRINDING CORN AND MAKING ETHANOL THEREFROM

CROSS-REFERENCE TO RELATED APPLICATIONS

This is a National Stage Application under 35 U.S.C. § 371 of PCT/US2016/063657, filed on Nov. 23, 2016, which claims priority to U.S. Provisional Patent Application No. 62/260,181, filed on Nov. 25, 2015, which are both incorporated by reference herein.

BACKGROUND

Field

Embodiments described generally relate to methods and systems for grinding corn and methods for making ethanol therefrom.

Description of the Related Art

Corn or maize is often used as a starch source to produce ethanol by fermentation. Corn is traditionally ground by a hammer mill in ethanol production facilities. Hammer milled corn has a very wide range of sizes and generally includes relatively large particle sizes.

The general consensus in the ethanol industry is that finer ground corn would be accompanied with too many problems during production of the ethanol. First, the low bulk density of finer ground corn would tend to form dust clouds when conveyed within the facility. Second, finer ground corn in ethanol production would increase the risk of forming "dough balls", which are lumps of corn flour that form in the slurry mixer and reduces or ceases production of ethanol. Third, finer ground corn would become entrained at the top of the stripper column leading to fouling and plugging of the rectifier. The finer ground corn would also reduce performance of the decanter centrifuge due to the lower sedimentation velocities of the smaller particles. As such, the solids content of the wet cake and the suspended solids content of the thin stillage would be greater and could require more energy to dry. In addition, the finer ground corn would increase fouling of the air to air heat exchanger in the dryer system causing increased downtime and requiring more frequent cleaning of the heat exchanger.

There is a need, therefore, for improved systems and methods for grinding corn and making ethanol therefrom.

SUMMARY

Processes for grinding corn, ground corn products, and processes for making ethanol from the ground corn products are provided herein. In some examples, a process for making ethanol can include introducing a plurality of corn pieces into a mill. The plurality of corn pieces can include whole corn kernels, fragmented corn kernels, size-reduced corn kernels, milled corn kernels, or any mixture thereof. The process can also include milling the corn pieces in the mill to produce a ground corn product. In Greater than 25 wt % of the ground corn product can have a particle size of greater than 105 µm, as measured according to AOAC 965.22-1966. Greater than 80 wt % of the ground corn product can have a particle size of 425 µm or less, as measured according to AOAC 965.22-1966. The process can also include processing the ground corn product to produce a fermentation mash that can include ethanol and separating at least a portion of the ethanol from the fermentation mash to produce a stillage.

In some examples, a process for making ethanol can include introducing a plurality of corn pieces into a mill. The plurality of corn pieces can include whole corn kernels, fragmented corn kernels, size-reduced corn kernels, milled corn kernels, or any mixture thereof. The process can also include milling the corn pieces in the mill to produce a ground corn product. The ground corn product can have a $d_{50}$ by volume percent of 100 µm to 400 µm, as measured according to ISO 13320:2009. The ground corn product can be processed to produce a fermentation mash that can include ethanol and separating at least a portion of the ethanol from the fermentation mash to produce a stillage.

In some examples, a process for making ethanol can include introducing a plurality of corn pieces into a mill. The plurality of corn pieces can include whole corn kernels, fragmented corn kernels, size-reduced corn kernels, milled corn kernels, or any mixture thereof. The mill can include a first rotatable disk and either a second rotatable disk or a stationary surface. A distance separating the first rotatable disk and either the second rotatable disk or the stationary surface can provide a shearing gap therebetween. The process can also include rotating the first rotatable disk and contacting the corn pieces to and shearing the corn pieces between the first rotatable disk and either the second rotatable disk or the stationary surface in the shearing gap to produce a ground corn product. Greater than 25 wt % of the ground corn product can have a particle size of greater than 105 µm, as measured according to AOAC 965.22-1966. Greater than 80 wt % of the ground corn product can have a particle size of 425 µm or less, as measured according to AOAC 965.22-1966. The ground corn product can be processed to produce a fermentation mash that can include ethanol and separating at least a portion of the ethanol from the fermentation mash to produce a stillage.

DETAILED DESCRIPTION

Figures 1, 2:
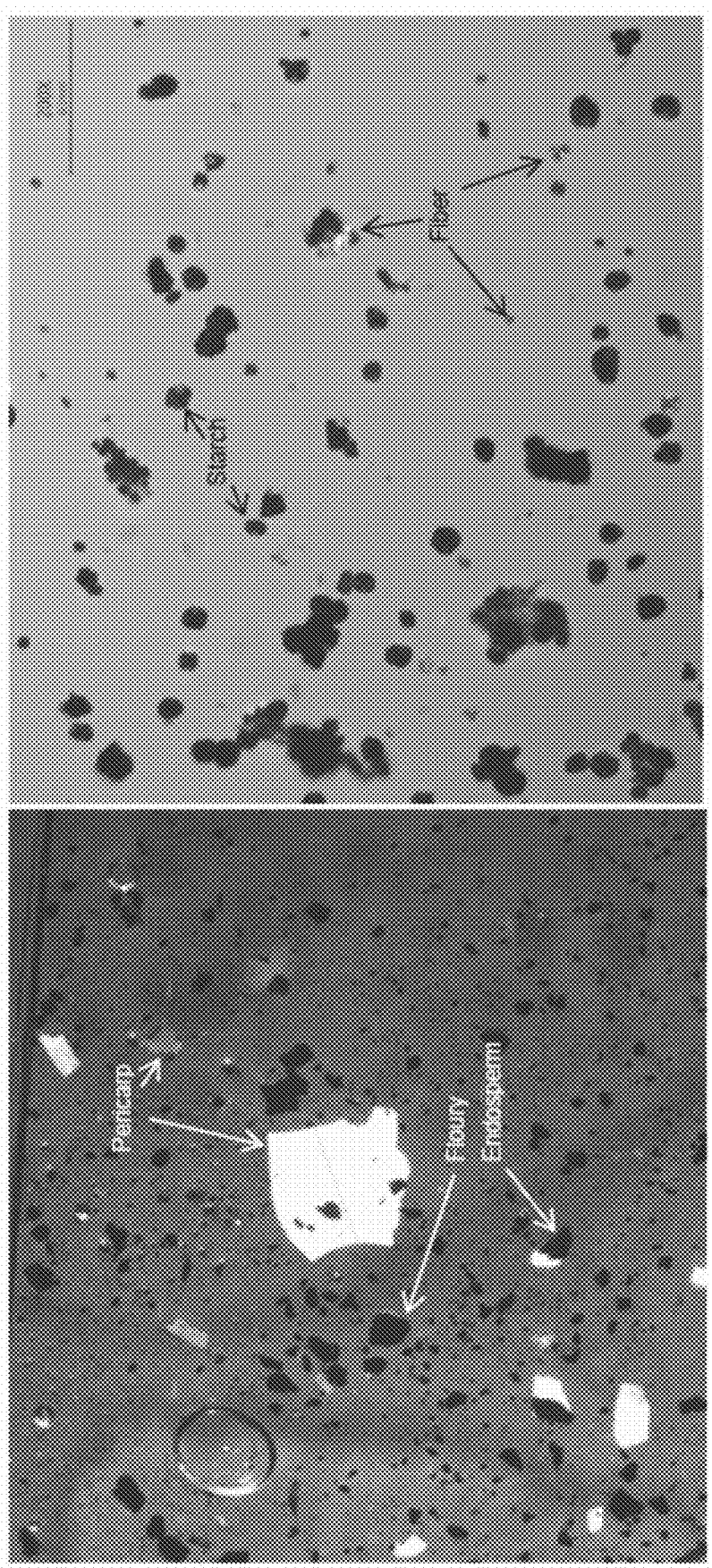
FIG. 1 is an optical microscope image of hammer milled corn (Comparative Example 1) at a magnification of 10×.
FIG. 2 is an optical microscope image of hammer milled corn (Comparative Example 1) at a magnification of 200×.

A ground corn product can be processed to produce a fermentation mash that contains ethanol. The ethanol can be distilled or otherwise removed from the fermentation mash to produce a stillage. The ground corn product can have a particle size of less than a particle size of conventional ground corn, e.g., hammer milled corn or roller milled corn. For example, the ground corn product can have a $d_{50}$ of about 100 μm to about 500 μm, as measured according to ISO 13320:2009. In contrast, hammer milled corn can have a $d_{50}$ of greater than 500 μm and roller milled corn can have a $d_{50}$ of greater than 600 μm.

In some examples, greater than 25 wt % of the ground corn product can have a particle size of greater than 105 μm and greater than 80 wt % of the ground corn product can have a particle size of 425 μm or less, as measured according to AOAC 965.22-1966. The particle size distribution of the ground corn product produced in the high shear mill is further discussed and described below. It has been surprisingly and unexpectedly discovered that when 80 wt % or more of the ground corn product has a particle size of 425 μm or less and when greater than 25 wt % of the ground corn product has a particle size of greater than 105 μm, one or more product yields (e.g., corn oil) and/or one or more system efficiencies is realized as compared to conventional ethanol production processes that use a ground corn in which less than 80 wt % of the ground corn has a particle size of 425 μm or less or when less than 25 wt % (e.g., less than 20 wt %) of the ground corn product has a particle size of greater than 105 μm.

The ground corn product can be milled from a plurality of corn pieces by one or more high shear mills. The corn pieces can be or include, but are not limited to, whole corn kernels, fragmented corn kernels, size-reduced corn kernels, milled corn kernels, ground corn kernels, fresh corn kernels, dried corn kernels, or any mixture thereof. In some examples, whole corn kernels can be size-reduced via one or more non-high shear mills, such as one or more hammer mills and/or one or more roller mills using a non-shearing technique, to produce a coarsely ground corn. The coarse ground corn can be further size-reduced, such as sheared, milled, or otherwise ground, in the one or more high shear mills to produce the ground corn product. The high shear mill can be or include, but is not limited to, one or more of: disk mill fiberizers, air swept pulverizers, other high shear mills, or any combination thereof.

The ground corn product produced in the high shear mill can be processed or otherwise treated in one or more process units to produce a fermentation mash. The process units can include one or multiple vessels and/or apparatuses, such as slurry tanks and/or liquefaction tanks, for heating, mixing, separating, and/or carrying out other operations to the slurry. In some examples, the ground corn product can be transferred from the high shear mill to one or more slurry tanks. Other components or products from downstream of the ethanol process can also be combined with the ground corn product in the slurry tanks. The ground corn product can be mixed, blended, or otherwise combined with water, one or more enzymes, such as alpha-amylase, one or more optional additives, and one or more optional recycled downstream components to produce a slurry tank mixture. The slurry tank mixture can be processed to produce the fermentation mash. The slurry tank mixture can be heated to produce a gelatinized starch. The gelatinized starch can be hydrolyzed to produce a liquefaction mash. The liquefaction mash can be subjected to saccharification and fermentation to produce the fermentation mash.

The slurry tank mixture can be heated in a cooker (e.g., a pressurized jet cooker) to solubilize the starch in the ground corn product to produce a solubilized mixture of starch gelatinization. The slurry tank mixture can be mixed using a paddle mixer, a ribbon blender, or a dense phase slurry mixer. The slurry tank mixture can be heated to a temperature that is at or above the onset of gelatinization where the alpha amylase can solubilize the starch. In one example, the temperature can be above the temperature where the onset of gelatinization occurs, but below the temperature needed to complete gelatinization. The starch is hydrolyzed by the enzyme into maltodextrins and oligosaccharides. Given sufficiently small particle size the hydrolysis can occur without complete gelatinization. Lower temperature liquefaction offers the benefit of reduced energy use and reduced damage to starch due to undesirable side reactions such as the Maillard reaction as well as reduce the formation of "dough balls" as discussed above. In some examples, the slurry tank can be heated to a lower temperature than the onset of gelatinization as indicated in U.S. Pat. No. 7,842,484, which is herein incorporated by reference.

The slurry tank mixture can be heated to a temperature of than 90° C., less than 85° C., less than 80° C., less than 75° C., less than 72° C., or less than 70° C. The slurry tank mixture can be heated to a temperature of greater than 50° C., greater than 55° C., greater than 60° C., greater than 62° C., greater than 64° C., or greater than 66° C. to less than 70° C., less than 72° C., less than 75° C., less than 80° C., less than 85° C. or less than 90° C. For example, the slurry tank mixture can be heated to a temperature of greater than 50° C. to less than 90° C., greater than 55° C. to less than 90° C., greater than 60° C. to less than 90° C., greater than 55° C. to less than 85° C., greater than 55° C. to less than 80° C., greater than 60° C. to less than 90° C., greater than 60° C. to less than 85° C., greater than 65° C. to less than 90° C., greater than 65° C. to less than 85° C.

The solubilized mixture can be transferred from the slurry tank to one or more liquefaction tanks. One or more enzymes, such as alpha-amylase, can be added to the slurry in a liquefaction process to produce a liquefaction mash containing a hydrolyzed mixture. The enzyme (e.g., alpha-amylase) can hydrolyze the gelatinized starch into maltodextrins and oligosaccharides.

The liquefaction mash containing the hydrolyzed mixture can be further processed in one or more saccharification and fermentation processes to produce the fermentation mash. The saccharification and fermentation can occur sequentially or simultaneously. During saccharification, the liquefied mash can be cooled and one or more enzymes, such as glucoamylase, can be added to hydrolyze the maltodextrins and oligosaccharides into single glucose sugar molecules. During fermentation, one or more strains of yeast, such as *Saccharomyces cerevisae*, can be added to metabolize the glucose sugars into ethanol and carbon dioxide. After saccharification and fermentation, in some examples, the fermentation mash can include about 15 vol % to about 25 vol % of ethanol (volume/volume basis), as well as soluble and insoluble solids from remaining grain components, including, but not limited to, fibers, oils, and proteins.

The fermentation mash can be pumped or otherwise transferred from the fermenter or other process unit to one or more distillers where the fermentation mash can be heated to vaporize at least a portion of the ethanol. The distiller can be or include, but is not limited to, one or more distillation columns, distillation trains, or other devices configured to vaporize the ethanol. The ethanol can be distilled or otherwise separated from the fermentation mash within the distiller to produce a stillage. The stillage can include, but is not limited to, water insoluble solids (e.g., fiber particles), water soluble solids (e.g., starches), oils, and proteins.

The vaporized ethanol can be condensed in a condenser within or outside of the distiller and liquid alcohol (in this example, ethanol) can be recovered at about 95 vol % purity (190 proof). The 190 proof ethanol can be transferred into one or more dehydrators and dried. The dehydrator can be or include one or more dehydration columns, such as molecular sieve dehydration columns. The 190 proof ethanol can pass through the dehydration column in the dehydrator that can remove residual water from the ethanol, to yield a drier product of purified ethanol, such as about 99.75 vol % of ethanol (about 199.5 proof) that can be transferred to one or more ethanol storage containers. The stillage left in the distiller can be further processed to make a variety of products. Other illustrative products that can be derived from the stillage left in the distiller can include, but are not limited to, other alcohols, corn oil, distillers grains, protein products, and other products from corn stillage.

The ground corn product can be quantified by having a particle size distribution, such as by weight percent (wt %) and/or volume percent (vol %), for specified particle sizes. The particle size and the particle size distribution of the ground corn product can be analyzed or otherwise determined by various particle size analyzers, such as laser diffraction analyzers, static and/or dynamic light scattering analyzers, zeta potential analyzers, sieve shaker with graduation test, and others. Generally, the particle size distribution of the ground corn product by weight can be measured using sieves and the particle size distribution of the ground corn product by volume can be measured by laser diffraction, as further discussed and described below.

The particle size and the particle size distribution of the ground corn product by weight can be measured or otherwise determined with a sieve shaker, such as the RO-TAP® RX-29 sieve shaker, commercially available from W. S. Tyler Industrial Group. The sieves analysis can be performed according to the AOAC Official Method 965.22-1966 "Sorting Corn Grits—Sieving Method," available from AOAC International. Sieve sizes of 850 µm, 425 µm, 250 µm, 180 µm, 150 µm, and 105 µm can be used to categorize the particle size distribution of the ground corn product by weight.

The amount of the ground corn product that can have a particle size of 105 µm or less can be about 30 wt %, about 35 wt %, or about 40 wt % to about 45 wt %, about 50 wt %, about 55 wt %, about 60 wt %, about 65 wt %, about 70 wt %, about 75 wt %, or greater, as measured according to AOAC 965.22-1966. For example, about 32 wt % to about 68 wt %, about 41 wt % to about 66 wt %, about 32 wt % to about 62 wt %, or about 35 wt % to about 58 wt % of the ground corn product can have a particle size of 105 µm or less, as measured according to AOAC 965.22-1966. In some examples, greater than 30 wt %, greater than 35 wt %, greater than 40 wt %, greater than 45 wt %, greater than 50 wt %, greater than 55 wt %, greater than 60 wt %, greater than 65 wt %, or greater than 70 wt % of the ground corn product can have a particle size of 105 µm or less, as measured according to AOAC 965.22-1966. In other examples, greater than 25 wt %, greater than 30 wt %, greater than 35 wt %, greater than 40 wt %, greater than 45 wt %, or greater than 50 wt % to about 55 wt %, about 60 wt %, about 65 wt %, or about 70 wt % of the ground corn product can have a particle size of greater than 105 µm, as measured according to AOAC 965.22-1966.

The amount of the ground corn product that can have a particle size of 150 µm or less can be about 41 wt % to about 79 wt %, about 57 wt % to about 90 wt %, about 57 wt % to about 78 wt %, or about 57 wt % to about 75 wt %, as measured according to AOAC 965.22-1966. In some examples, greater than 40 wt %, greater than 50 wt %, greater than 60 wt %, greater than 70 wt %, greater than 75 wt %, or greater than 80 wt % of the ground corn product can have a particle size of 150 µm or less, as measured according to AOAC 965.22-1966.

The amount of the ground corn product that can have a particle size of 180 µm or less can be about 52 wt % to about 97 wt %, about 58 wt % to about 90 wt %, about 56 wt % to about 81 wt %, or about 62 wt % to about 97 wt %, as measured according to AOAC 965.22-1966. In some examples, greater than 50 wt %, greater than 60 wt %, greater than 70 wt %, greater than 80 wt %, greater than 90 wt %, greater than 93 wt %, greater than 95 wt %, or greater than 97 wt % of the ground corn product can have a particle size of 180 µm or less, as measured according to AOAC 965.22-1966.

The amount of the ground corn product that can have a particle size of 250 µm or less can be about 71 wt % to about 98 wt %, about 81 wt % to about 98 wt %, about 91 wt % to about 98 wt %, or about 71 wt % to about 92 wt %, as measured according to AOAC 965.22-1966. In some examples, greater than 70 wt %, greater than 80 wt %, greater than 85 wt %, greater than 90 wt %, greater than 93 wt %, greater than 95 wt %, greater than 96 wt %, greater than 97 wt %, or greater than 98 wt % of the ground corn product can have a particle size of 250 µm or less, as measured according to AOAC 965.22-1966.

The amount of the ground corn product that can have a particle size of 425 µm or less can be about 87 wt % to about 96 wt %, about 87 wt % to about 95 wt %, about 87 wt % to about 99.9 wt %, or about 96 wt % to about 99.9 wt %, as measured according to AOAC 965.22-1966. In some examples, greater than 85 wt %, greater than 90 wt %, greater than 93 wt %, greater than 95 wt %, greater than 96 wt %, greater than 97 wt %, greater than 98 wt %, greater than 99 wt %, greater than 99.5 wt %, greater than 99.7 wt %, or greater than 99.9 wt % of the ground corn product can have a particle size of 425 µm or less, as measured according to AOAC 965.22-1966. In other examples, greater than 80 wt %, greater than 83 wt %, greater than 85 wt %, greater than 87 wt %, greater than 90 wt %, greater than 93 wt %, or greater than 95 wt % of the ground corn product can have a particle size of 425 µm or less, as measured according to AOAC 965.22-1966. In some examples 100% of the ground corn product can have a particle size of 425 µm or less.

The amount of the ground corn product that can have a particle size of 850 µm or less can be about 98 wt % to about 99.95 wt %, about 99.2 wt % to about 99.9 wt %, about 99.2 wt % to about 99.95 wt %, or about 99.9 wt % to about 99.95 wt %, as measured according to AOAC 965.22-1966. In some examples, greater than 97 wt %, greater than 98 wt %, greater than 99 wt %, greater than 99.3 wt %, greater than 99.5 wt %, greater than 99.7 wt %, greater than 99.9 wt %, greater than 99.91 wt %, greater than 99.93 wt %, or greater than 99.95 wt % of the ground corn product can have a particle size of 850 µm or less, as measured according to AOAC 965.22-1966.

In one or more examples, about 30 wt % to about 65 wt % of the ground corn product can have a particle size of 105 µm or less; about 40 wt % to about 80 wt % of the ground corn product can have a particle size of 150 µm or less; about 50 wt % to about 97 wt % of the ground corn product can have a particle size of 180 µm or less; about 70 wt % to about 98 wt % of the ground corn product can have a particle size of 250 µm or less; about 85 wt % to about 99.9 wt % of the ground corn product can have a particle size of 425 µm or less; and about 98 wt % to about 99.95 wt % of the ground corn product can have a particle size of 850 μm or less, as measured according to AOAC 965.22-1966. For example, greater than 30 wt %, greater than 40 wt %, greater than 50 wt %, or greater than 60 wt % of the ground corn product can have a particle size of 105 μm or less; greater than 40 wt %, greater than 50 wt %, greater than 60 wt %, or greater than 70 wt % of the ground corn product can have a particle size of 150 μm or less; greater than 50 wt %, greater than 60 wt %, greater than 70 wt %, or greater than 80 wt % of the ground corn product can have a particle size of 180 μm or less; greater than 70 wt %, greater than 80 wt %, greater than 90 wt %, or greater than 95 wt % of the ground corn product for a particle size of 250 μm or less; greater than 85 wt %, greater than 90 wt %, greater than 95 wt %, greater than 97 wt %, greater than 99 wt %, greater than 99.5 wt %, or greater than 99.9 wt % of the ground corn product can have a particle size of 425 μm or less; greater than 98 wt %, greater than 99 wt %, greater than 99.5 wt %, greater than 99.9 wt %, greater than 99.93 wt %, or greater than 99.95 wt % of the ground corn product can have a particle size of 850 μm or less, as measured according to AOAC 965.22-1966. In at least one example, greater than 25 wt %, greater than 30 wt %, greater than 35 wt %, greater than 40 wt %, or greater than 45 wt % of the ground corn product can have a particle size of greater than 105 μm, and greater than 80 wt %, greater than 85 wt %, greater than 90 wt %, or greater than 95 wt % of the ground corn product can have a particle size of 425 μm or less, as measured according to AOAC 965.22-1966.

The particle size and the particle size distribution of the ground corn product by volume can be analyzed on a LS™ 13-320 laser diffraction particle size analyzer with a Tornado dry sample module attachment, both commercially available from Beckman Coulter Life Sciences. The laser diffraction particle analysis can be conducted according to the ISO 13320:2009 "Particle Size Analysis—Laser Diffraction Methods," available from International Organization for Standardization.

The amount of the ground corn product that can have a particle size of 25 μm or less can be about 2 vol % to about 10 vol %, about 2 vol % to about 9 vol %, about 2 vol % to about 8 vol %, or about 3 vol % to about 10 vol %, as measured according to ISO 13320:2009. In some examples, greater than 2 vol %, greater than 4 vol %, greater than 6 vol %, greater than 8 vol %, or greater than 9 vol % of the ground corn product can have a particle size of 25 μm or less, as measured according to ISO 13320:2009.

The amount of the ground corn product that can have a particle size of 60 μm or less can be about 16 vol % to about 24 vol %, about 19 vol % to about 25 vol %, about 16 vol % to about 26 vol %, or about 19 vol % to about 28 vol %, as measured according to ISO 13320:2009. In some examples, greater than 10 vol %, greater than 13 vol %, greater than 15 vol %, greater than 17 vol %, greater than 18 vol %, greater than 20 vol %, greater than 22 vol %, greater than 23 vol %, greater than 25 vol %, greater than 28 vol %, greater than t 30 vol %, greater than 35 vol % of the ground corn product can have a particle size of 60 μm or less, as measured according to ISO 13320:2009.

The amount of the ground corn product that can have a particle size of 400 μm or less can be about 42 vol % to about 74 vol %, about 42 vol % to about 71 vol %, about 59 vol % to about 71 vol %, or about 54 vol % to about 71 vol % of the ground corn product can have a particle size of 400 μm or less, as measured according to ISO 13320:2009. In some examples, greater than 40 vol %, greater than 45 vol %, greater than 50 vol %, greater than 55 vol %, greater than 60 vol %, greater than 65 vol %, or greater than 70 vol % of the ground corn product can have a particle size of 400 μm or less, as measured according to ISO 13320:2009.

The amount of the ground corn product that can have a particle size of 800 μm or less can be about 86 vol % to about 90 vol %, about 86 vol % to about 96 vol %, about 87 vol % to about 95 vol %, or about 87 vol % to about 96 vol %, as measured according to ISO 13320:2009. In some examples, greater than 85 vol %, greater than 87 vol %, greater than 89 vol %, greater than 90 vol %, greater than 93 vol %, greater than 94 vol %, or greater than 95 vol % of the ground corn product can have a particle size of 800 μm or less, as measured according to ISO 13320:2009.

In one or more examples, about 10 vol % to about 30 vol % of the ground corn product can have a particle size of 60 μm or less; about 40 vol % to about 70 vol % of the ground corn product can have a particle size of 400 μm or less; and about 85 vol % to about 95 vol % of the ground corn product can have a particle size of 800 μm or less. In other examples, greater than 10 vol %, greater than 15 vol %, greater than 18 vol %, greater than 20 vol %, greater than 25 vol %, greater than 28 vol %, or greater than 30 vol % of the ground corn product can have a particle size of 60 μm or less; greater than 40 vol %, greater than 50 vol %, greater than 55 vol %, greater than 60 vol %, or greater than 70 vol % of the ground corn product can have a particle size of 400 μm or less; and greater than 85 vol %, greater than 90 vol %, or greater than 95 vol % of the ground corn product can have a particle size of 800 μm or less. For example, greater than 18 vol % of the ground corn product can have a particle size of 60 μm or less and greater than 50 vol % of the ground corn product can have a particle size of 400 μm or less, as measured according to ISO 13320:2009.

In some examples, greater than 20 vol % of the ground corn product can have a particle size of 60 μm or less and greater than 60 vol % of the ground corn product can have a particle size of 400 μm or less, as measured according to ISO 13320:2009. In other examples, greater than 18 vol % of the ground corn product can have a particle size of 60 μm or less and greater than 85 vol % of the ground corn product can have a particle size of 800 μm or less, as measured according to ISO 13320:2009. In some examples, greater than 50 vol % of the ground corn product can have a particle size of 400 μm or less and greater than 85 vol % of the ground corn product can have a particle size of 800 μm or less, as measured according to ISO 13320:2009. In other examples, greater than 22 vol % of the ground corn product can have a particle size of 60 μm or less, greater than 60 vol % of the ground corn product having a particle size of 400 μm or less, and greater than 90 vol % of the ground corn product can have a particle size of 800 μm or less, as measured according to ISO 13320:2009.

The volumetric particle size distribution of the ground corn product can be provided by particle size, $d_v$, where v is the volume percent of the ground corn product that has a particle size smaller than the specified value. For example, if the ground corn product has a $d_{10}$ by volume percent of 18 μm, then 10 vol % of the ground corn product has a particle size of less than 18 μm and 90 vol % of the ground corn product has a particle size of 18 μm and larger. In another example, if the ground corn product has a $d_{50}$ by volume percent of 170 μm, then 50 vol % of the ground corn product has a particle size of less than 170 μm and 50 vol % of the ground corn product has a particle size of 170 μm and larger. In another example, if the ground corn product has a $d_{90}$ by volume percent of 800 μm, then 90 vol % of the ground corn product has a particle size of less than 800 µm and 10 vol % of the ground corn product has a particle size of 800 µm and larger.

The ground corn product can have a $d_{10}$ by volume percent of 5 µm, 10 µm, 12 µm, or 15 µm to 20 µm, 25 µm, 30 µm, 40 µm, or 50 µm, as measured according to ISO 13320:2009. For example, the ground corn product can have a $d_{10}$ by volume percent of 10 µm to 50 µm, 10 µm to 30 µm, 10 µm to 25 µm, 10 µm to 20 µm, 12 µm to 30 µm, 12 µm to 25 µm, 12 µm to 20 µm, 14 µm to 30 µm, 14 µm to 25 µm, 14 µm to 20 µm, 15 µm to 25 µm, 16 µm to 30 µm, or 16 µm to 25 µm, as measured according to ISO 13320:2009.

The ground corn product can have a $d_{25}$ by volume percent of 30 µm, 40 µm, or 50 µm to 55 µm, 60 µm, 70 µm, 80 µm, 90 µm, 100 µm, 110 µm, 120 µm, 130 µm, 140 µm, or 150 µm, as measured according to ISO 13320:2009. For example, the ground corn product can have a $d_{25}$ by volume percent of 30 µm to 120 µm, 30 µm to 110 µm, 30 µm to 101 µm, 30 µm to 93 µm, 30 µm to 88 µm, 30 µm to 75 µm, 30 µm to 66 µm, 30 µm to 55 µm, 40 µm to 120 µm, 40 µm to 101 µm, 40 µm to 93 µm, 40 µm to 88 µm, 40 µm to 75 µm, 40 µm to 66 µm, 40 µm to 55 µm, 40 µm to 48 µm, 50 µm to 120 µm, 50 µm to 110 µm, 50 µm to 101 µm, 50 µm to 97 µm, 50 µm to 93 µm, 50 µm to 75 µm, or 50 µm to 66 µm, as measured according to ISO 13320:2009.

The ground corn product can have a $d_{50}$ by volume percent of 100 µm, 110 µm, 120 µm, 125 µm, or 150 µm to 200 µm, 250 µm, 300 µm, 350 µm, 400 µm, 450 µm, or 500 µm, as measured according to ISO 13320:2009. For example, the ground corn product can have a $d_{50}$ by volume percent of 100 µm to 500 µm, 100 µm to 450 µm, 100 µm to 400 µm, 100 µm to 350 µm, 100 µm to 300 µm, 100 µm to 250 µm, 100 µm to 200 µm, 100 µm to 150 µm, 110 µm to 500 µm, 110 µm to 400 µm, 110 µm to 300 µm, 110 µm to 250 µm, 110 µm to 200 µm, 110 µm to 150 µm, 150 µm to 500 µm, 150 µm to 450 µm, 150 µm to 400 µm, 150 µm to 350 µm, 150 µm to 300 µm, 150 µm to 250 µm, 150 µm to 200 µm, or 150 µm to 175 µm, as measured according to ISO 13320:2009.

The ground corn product can have a $d_{75}$ by volume percent of 350 µm, 375 µm, 400 µm, or 425 µm to 450 µm, 500 µm, 550 µm, 600 µm, 650 µm, or 700 µm, as measured according to ISO 13320:2009. For example, the ground corn product can have a $d_{75}$ by volume percent of 350 µm to 700 µm, 350 µm to 650 µm, 350 µm to 600 µm, 350 µm to 550 µm, 350 µm to 500 µm, 350 µm to 450 µm, 350 µm to 400 µm, 375 µm to 700 µm, 375 µm to 600 µm, 375 µm to 500 µm, 375 µm to 450 µm, 375 µm to 400 µm, 400 µm to 700 µm, 400 µm to 600 µm, 400 µm to 500 µm, 425 µm to 700 µm, 425 µm to 650 µm, 425 µm to 600 µm, 425 µm to 550 µm, or 425 µm to 500 µm, as measured according to ISO 13320:2009.

The ground corn product can have a $d_{90}$ by volume percent of 650 µm, 700 µm, 750 µm, or 800 µm to 850 µm, 900 µm, 950 µm, 1,000 µm, 1,050 µm, or 1,100 µm, as measured according to ISO 13320:2009. For example, the ground corn product can have a $d_{90}$ by volume percent of 650 µm to 1,100 µm, 675 µm to 1,100 µm, 700 µm to 1,100 µm, 725 µm to 1,100 µm, 750 µm to 1,100 µm, 800 µm to 1,100 µm, 850 µm to 1,100 µm, 650 µm to 1,000 µm, 675 µm to 1,000 µm, 700 µm to 1,000 µm, 725 µm to 1,000 µm, 750 µm to 1,000 µm, 800 µm to 1,000 µm, 850 µm to 1,000 µm, 650 µm to 950 µm, 700 µm to 950 µm, 725 µm to 950 µm, 750 µm to 950 µm, 800 µm to 950 µm, 850 µm to 950 µm, 650 µm to 900 µm, 675 µm to 900 µm, 700 µm to 900 µm, 750 µm to 900 µm, 800 µm to 900 µm, 650 µm to 850 µm, 675 µm to 850 µm, 700 µm to 850 µm, or 750 µm to 850 µm, as measured according to ISO 13320:2009.

The ground corn product can include, but is not limited to, pericarp particles, floury endosperm particles, germ particles, starch particles, and fiber particles. The starch portions and the germ portions of the corn kernels can be size-reduced to smaller sizes than the fibrous portions of the corn kernels. It is believed that this difference in sizes of the corn portions is a result of the shearing action of the milling device (e.g., air swept pulverizer or disk mill fiberizer). The ground corn product, therefore, can include fiber particles with different particle size distributions than the total particles of the ground corn product.

In one or more examples, the fiber particles of the ground corn product can have a $d_{50}$ by volume percent of 125 µm, 150 µm, or 250 µm to 300 µm, 400 µm, or 500 µm and the total particles of the ground corn product can have a $d_{50}$ by volume percent of 100 µm, 125 µm, or 150 µm to 200 µm, 300 µm, 400 µm, or 500 µm, as measured according to ISO 13320:2009. For example, the fiber particles of the ground corn product can have a $d_{50}$ by volume percent of 125 µm to 450 µm, 150 µm to 450 µm, or 175 µm to 400 µm and the total particles of the ground corn product can have a $d_{50}$ by volume percent of 100 µm to 400 µm, 100 µm to 350 µm, or 125 µm to 300 µm, as measured according to ISO 13320:2009.

In one or more examples, a plurality of total particles of the ground corn product can include a plurality of fiber particles. The fiber particles in the ground corn product can have a $d_{50}$ by volume percent of greater than 200 µm, greater than 250 µm, greater than 300 µm, or greater than 350 µm to 500 µm and the total particles of the ground corn product can have a $d_{50}$ by volume percent of 100 µm to less than 300 µm, less than 350 µm, less than 450 µm, or less than 500 µm, as measured according to ISO 13320:2009. For example, the fiber particles of the ground corn product can have a $d_{50}$ by volume percent of greater than 200 µm and the total particles of the ground corn product can have a $d_{50}$ by volume percent of less than 500 µm, as measured according to ISO 13320:2009. In another example, the fiber particles of the ground corn product can have a $d_{50}$ by volume percent of greater than 250 µm and the total particles of the ground corn product can have a $d_{50}$ by volume percent of less than 450 µm, as measured according to ISO 13320:2009. In some examples, the fiber particles of the ground corn product can have a $d_{50}$ by volume percent of greater than 300 µm and the total particles of the ground corn product can have a $d_{50}$ by volume percent of less than 400 µm, as measured according to ISO 13320:2009. In other examples, the fiber particles of the ground corn product can have a $d_{50}$ by volume percent of greater than 350 µm and the total particles of the ground corn product can have a $d_{50}$ by volume percent of less than 350 µm, as measured according to ISO 13320:2009. In other examples, the fiber particles of the ground corn product can have a $d_{50}$ by volume percent of greater than 200 µm to 500 µm and the total particles of the ground corn product can have a $d_{50}$ by volume percent of 100 µm to less than 500 µm, as measured according to ISO 13320:2009.

In other examples, the fiber particles of the ground corn product can have a $d_{75}$ by volume percent of 375 µm, 400 µm, or 450 µm to 500 µm, 600 µm, or 700 µm and the total particles of the ground corn product can have a $d_{75}$ by volume percent of 350 µm, 400 µm, or 425 µm to 450 µm, 500 µm, 600 µm, or 700 µm, as measured according to ISO 13320:2009. For example, the fiber particles of the ground corn product can have a $d_{75}$ by volume percent of 375 µm to 700 µm, 400 µm to 600 µm, or 450 µm to 700 µm and the total particles of the ground corn product can have a $d_{75}$ by volume percent of 350 μm to 600 μm, 350 μm to 500 μm, or 325 μm to 550 μm, as measured according to ISO 13320: 2009.

It should be understood that the ground corn product or any portion thereof (e.g., fiber particles) can have a combination of any two or more properties discussed and described above or elsewhere herein. For example, the ground corn product can have a combination of any two, any three, any four, or more, of the following properties: the particle size by weight, the particle size by volume, the particle size distribution by weight, the particle size distribution by volume, the $d_{10}$ value, the $d_{25}$ value, the $d_{50}$ value, the $d_{75}$ value, the $d_{90}$ value, and the crystallinity, which are discussed and described above or elsewhere herein.

The ground corn product and the corn pieces (e.g., corn kernels) from which the ground corn product is ground can have the same composition or substantially the same composition. The corn pieces and the ground corn product can contain, but are not limited to, water, one or more starches (e.g., saccharides and oligosaccharides), one or more proteins, cellulose, one or more oils and/or greases (e.g., saturated and unsaturated fatty acids), one or more volatile organic compounds, other components, or any combination thereof. Generally, for example, the corn pieces and the ground corn product can each include about 5 wt % to about 40 wt % of water, about 15 wt % to about 25 wt % of oligosaccharides, and about 0.5 wt % to about 5 wt % of corn oil.

The corn oil can be or include one or more oils and/or one or more greases which can include one or more saturated fatty acids and/or one or more unsaturated fatty acids. Illustrative saturated fatty acids and unsaturated fatty acids that can be contained in the corn pieces and the ground corn product can be or include caprylic acid, capric acid, myristic acid, palmitic acid, stearic acid, arachidic acid, oleic acid, linoleic acid, linolenic acid, isomers thereof, or any mixture thereof. For example, the corn oil can include about 10 wt % to about 15 wt % of palmitic acid, about 1 wt % to about 2 wt % of stearic acid, about 0.5 wt % to about 2 wt % of arachidic acid, about 20 wt % to about 40 wt % of oleic acid, about 45 wt % to about 65 wt % of linoleic acid, and about 0.5 wt % to about 2 wt % of linolenic acid.

The corn pieces and the ground corn product can include about 0.5 wt %, about 0.8 wt %, about 1 wt %, about 1.5 wt %, or about 1.8 wt % to about 2 wt %, about 2.2 wt %, about 2.5 wt %, about 2.7 wt %, about 3 wt %, about 3.2 wt %, about 3.5 wt %, about 3.7 wt %, about 4 wt %, about 4.5 wt %, or more of corn oil, based on a solids weight of the corn pieces or the ground corn product. For example, the corn pieces and the ground corn product can include about 0.5 wt % to about 4.5 wt %, about 0.5 wt % to about 4 wt %, about 0.5 wt % to about 3.5 wt %, about 0.5 wt % to about 3 wt %, about 0.5 wt % to about 2.5 wt %, about 0.5 wt % to about 2 wt %, about 0.5 wt % to about 1.5 wt %, about 0.5 wt % to about 1 wt %, about 1 wt % to about 4.5 wt %, about 1 wt % to about 4 wt %, about 1 wt % to about 3.5 wt %, about 1 wt % to about 3 wt %, about 1 wt % to about 2.5 wt %, about 1 wt % to about 2 wt %, about 1 wt % to about 1.5 wt %, about 1 wt % to about 1.3 wt %, about 2 wt % to about 4.5 wt %, about 2 wt % to about 4 wt %, about 2 wt % to about 3.5 wt %, about 2 wt % to about 3 wt %, about 2 wt % to about 2.5 wt %, about 2 wt % to about 2.3 wt %, about 2.5 wt % to about 4.5 wt %, about 2.5 wt % to about 4 wt %, about 2.5 wt % to about 3.5 wt %, about 2.5 wt % to about 3 wt %, about 2.5 wt % to about 2.8 wt %, about 3 wt % to about 4.5 wt %, about 3 wt % to about 4 wt %, about 3 wt % to about 3.7 wt %, about 3 wt % to about 3.5 wt %, or about 3 wt % to about 3.2 wt % of corn oil, based on a solids weight of the corn pieces or the ground corn product.

In one or more examples, the corn pieces and the ground corn product can include about 5 wt % to about 40 wt % of water, about 15 wt % to about 25 wt % of soluble starches, about 5 wt % to about 15 wt % of cellulose, and about 0.5 wt % to about 4 wt % of corn oil, based on a solids weight of the corn pieces or the ground corn product. In some examples, the corn pieces and the ground corn product can include about 10 wt % to about 35 wt % of water, about 17 wt % to about 28 wt % of soluble starches, about 10 wt % to about 15 wt % of cellulose, and about 2 wt % to about 4 wt % of corn oil, based on a solids weight of the corn pieces or the ground corn product.

Corn pieces (e.g., corn kernels) can be milled, ground, pulverized, fiberized, or otherwise size-reduced to produce the ground corn product. The corn pieces can also be milled, ground, pulverized, fiberized, or otherwise size-reduced two, three, or more times to produce the ground corn product. The plurality of corn pieces, therefore, can be or include size-reduced corn that is further size-reduced to produce the ground corn product. Illustrative corn pieces that are suitable to be size-reduced can be or include, but are not limited to, whole corn kernels, milled corn kernels, pulverized corn kernels, fiberized corn kernels, ground corn kernels, fragmented corn kernels, crushed corn kernels, smashed corn kernels, shredded corn kernels, other size-reduced corn kernels, fresh corn kernels, dried corn kernels, or any mixture thereof.

In some examples, the corn pieces (e.g., corn kernels) can be size-reduced one or more times with a hammer mill, a roller mill, or other type of mill to produce the plurality of corn pieces that can be further size-reduced one or more times with a high shear mill to produce the ground corn product. For example, the corn pieces can be passed through a hammer mill to produce size-reduced corn that subsequently can be passed through a disk mill fiberizer, an air swept pulverizer, and/or any other high shear mills to produce the ground corn product. The ground corn product can be or include fiberized corn, pulverized corn, disk milled corn, other high shear milled corn, or any mixtures thereof.

The corn pieces can be introduced to a high shear mill that can have two rotating surfaces, such as a first rotatable disk and a second rotatable disk. In other examples, the corn pieces can be introduced to a high shear mill that can have one rotating surface and one stationary surface, such as one rotatable disk and one stationary disk, plate, or other surface. The corn pieces can make contact to the two rotating surfaces or can make contact to the one rotating surface and the one stationary surface to mill, shear, grind, fiberize, pulverize, or otherwise size-reduce the corn pieces between the two rotating surfaces or between the one rotating surface and the one stationary surface to produce the ground corn product. For example, the high shear mill can be a disk attrition mill and the corn pieces can be milled or otherwise side-reduced between: a rotatable disk and a stationary disk; a rotatable disk and a stationary surface; or two rotatable disks to produce the ground corn product. In some examples, the corn pieces can be fiberized between two sets of triangular teeth, relatively sharp teeth, or fiberizing teeth of the disk attrition mill to produce fiberized corn product. In other examples, the corn pieces can be pulverized between two sets of rectangular teeth, relatively dull teeth, or pulverizing teeth of the disk attrition mill to produce pulverized corn product. In some examples, at least one disk can have grinding teeth for fiberizing the corn pieces into the ground corn product. Various disk attrition mills can be used to fiberize and/or pulverize. Some disk attrition mills can have a fiberizing side and a pulverizing side which are independent from each other. Disk attrition mills that can be used to mill, grind, or otherwise size-reduce corn can include, for example, the 66 inch fiberizer, commercially available from Reynolds Engineering and Equipment, Inc.

In one or more examples, the corn pieces can be introduced into a disk attrition mill, such as a high shear fiberizer or a high shear pulverizer. The disk attrition mill can include a first rotatable disk and either a second rotatable disk or a stationary surface. The disk attrition mill can have at least one set of grinding teeth disposed on each of the first rotatable disk, the second rotatable disk, and the stationary surface. In some configurations, any of the first rotatable disk, the second rotatable disk, or the stationary surface can be free of grinding teeth. In some examples of the disk attrition mill, the first rotatable disk can have a first set of grinding teeth and either the second rotatable disk or the stationary surface is free of grinding teeth. In other examples of the disk attrition mill, the first rotatable disk can have a first set of grinding teeth and either the second rotatable disk or the stationary surface can have a second set of grinding teeth.

The first rotatable disk and either the second rotatable disk or the stationary surface can be separated by a predetermined distance from each other to provide a shearing gap therebetween. The predetermined distance can be fixed or adjustable. If the first rotatable disk and/or either the second rotatable disk or the stationary surface have one or more sets of grinding teeth, then the shearing gap can be measured by the distance between two sets of grinding teeth or between one set of grinding teeth and either the rotatable disk or the stationary surface. For example, the shearing gap can be measured by the distance between the first set of grinding teeth on the first rotatable disk and the second set of grinding teeth on either the second rotatable disk or the stationary surface. In another example, the shearing gap can be measured by the distance between the first set of grinding teeth on the first rotatable disk and either the second rotatable disk or the stationary surface absent of grinding teeth. The shearing gap can be adjusted and/or can be maintained before and/or during the milling of the corn particles to produce the ground corn product. The shearing gap can be adjusted to produce the ground corn product having the particle size of the ground corn product and a desired distribution of the particle size of the ground corn product. Once the ground corn product is produced within the shearing gap, the ground corn product can pass through the shearing gap to exit the disk mill.

The shearing gap or the distance between the first rotatable disk and/or either the second rotatable disk or the stationary surface can be less than 3,000 µm, less than 2,600 µm, less than 2,000 µm, less than 1,500 µm, less than 1,000 µm, less than 800 µm, less than 500 µm, or less than 250 µm. The shearing gap or the distance between the first rotatable disk and/or either the second rotatable disk or the stationary surface can be about 50 µm, about 100 µm, about 150 µm, or about 250 µm to about 300 µm, about 500 µm, about 700 µm, about 800 µm, about 1,000 µm, about 1,500 µm, about 2,000 µm, about 2,500 µm, or about 2,750 µm. For example, the shearing gap or the distance between the first rotatable disk and/or either the second rotatable disk or the stationary surface can be about 250 µm to about 3,000 µm, about 400 µm to about 2,000 µm, about 500 µm to about 1,000 µm, about 700 µm to about 800 µm, about 700 µm to about 2,800 µm, or about 600 µm to about 2,600 µm.

The corn pieces can be ground, milled, fiberized, pulverized, or otherwise size-reduced to produce the ground corn product that maintains at least a substantial amount of the crystallinity relative to the corn pieces ground to produce the ground corn product. The ground corn product can have a crystallinity that is greater than 75%, about 80%, about 85%, or about 90% to about 92%, about 94%, about 95%, about 96%, about 97%, about 98%, about 99%, about 99.2%, about 99.5%, about 99.7%, about 99.8%, about 99.9%, about 99.95%, about 99.97%, about 99.98%, about 99.99%, or 100%, as compared to the crystallinity of the corn pieces ground to produce the ground corn product. For example, the ground corn product can have a crystallinity that is greater than 75%, greater than 80%, greater than 85%, greater than 90%, greater than 92%, greater than 94%, greater than 95%, greater than 96%, greater than 97%, greater than 98%, greater than 99%, greater than 99.2%, greater than 99.5%, greater than 99.7%, greater than 99.8%, greater than 99.9%, greater than 99.95%, greater than 99.97%, greater than 99.98%, greater than 99.99%, or 100%, as compared to the crystallinity of the corn pieces ground to produce the ground corn product.

For example, the ground corn product can have a crystallinity that is about 80% to 100%, about 85% to 100%, about 90% to 100%, about 95% to 100%, about 97% to 100%, about 98% to 100%, about 99% to 100%, about 99.5% to 100%, about 99.9% to 100%, about 99.95% to 100%, about 75% to about 99%, about 80% to about 99%, about 85% to about 99%, about 90% to about 99%, about 95% to about 99%, about 97% to about 99%, about 98% to about 99%, or about 98.5% to about 99%, as compared to the crystallinity of the corn pieces ground to produce the ground corn product. In other examples, the ground corn product can have a crystallinity that is greater than 75% to 100%, greater than 80% to 100%, greater than 85% to 100%, greater than 90% to 100%, greater than 95% to 100%, greater than 97% to 100%, greater than 98% to 100%, greater than 99% to 100%, greater than 99.5% to 100%, greater than 99.9% to 100%, greater than 99.95% to 100%, greater than 75% to about 99%, greater than 80% to about 99%, greater than 85% to about 99%, greater than 90% to about 99%, greater than 95% to about 99%, greater than 97% to about 99%, greater than 98% to about 99%, or greater than 98.5% to about 99%, as compared to the crystallinity of the corn pieces ground to produce the ground corn product.

The ground corn product can have a crystallinity that is reduced by less than 25%, less than 23%, less than 20%, less than 17%, less than 15%, less than 12%, less than 10%, less than 8%, less than 6%, less than 5%, less than 4%, less than 3%, less than 2%, less than 1%, less than 0.8%, less than 0.5%, less than 0.3%, less than 0.2%, less than 0.1%, less than 0.05%, less than 0.03%, or less than 0.01%, as compared to the crystallinity of the corn pieces ground to produce the ground corn product. For example, the ground corn product can have a crystallinity that is reduced by less than 25% to about 0.001%, less than 25% to about 0.01%, less than 25% to about 0.05%, less than 25% to about 0.1%, less than 10% to about 0.001%, less than 10% to about 0.01%, less than 10% to about 0.05%, less than 10% to about 0.1%, less than 5% to about 0.001%, less than 5% to about 0.01%, less than 5% to about 0.05%, less than 5% to about 0.1%, less than 1% to about 0.001%, less than 1% to about 0.01%, less than 1% to about 0.05%, less than 1% to about 0.1%, less than 0.1% to about 0.001%, less than 0.1% to about 0.01%, less than 0.1% to about 0.08%, or less than 0.1% to about 0.04%, as compared to the crystallinity of the corn pieces ground to produce the ground corn product.

As used herein, the term "crystallinity" refers to a volume ratio of the crystalline portion of cellulose to the total volume of cellulose that includes both the amorphous portion and the crystalline portion. The degree of crystallinity of the ground corn product can be calculated from X-ray diffraction (XRD) data by using a crystalline area integration method based on Cheetham and Leping (Carbohydrate Polymers 36:277-284 (1998)); Nara et al. (Starch 35, 12:407-410 (1983)); and Benedetti et al. (Journal of Material Science 18.4:1039-1048 (1983)). The intensities are first normalized over a limited range of data (10-30 2-theta). The normalization is determined by a baseline connecting the upper and lower bounds of 10 and 30 2-theta and then dividing the intensities by the integrated area below the intensities curve and above the baseline. After normalization, a Savitzky-Golay filter is used to smooth the data. The crystalline and amorphous regions can be separated by a function that connects peak baselines. The crystalline portion is the upper region and the amorphous portion is the lower region. The crystalline portion area and the total diffraction area are integrated. The degree of crystallinity is defined as the ratio of the crystalline area over the total diffraction area.

At least a portion of the corn oil can be extracted or otherwise removed from the ground corn product. For example, corn oil can be extracted or otherwise removed from the ground corn product, the slurry tank mixture containing the ground corn product, the liquefaction mash derived from the ground corn product, the fermentation mash, and/or the stillage. In some examples, the portion of the corn oil that is extracted from the ground corn product is the oil liberated from the corn cellular matrix within the ground corn product and any other oil that is bound by the corn cellular matrix remains in the ground corn product. The corn oil extraction and the corn oil testing can be performed on the SPE-DEX® 3000XL Automated Extractor System and the SPEED-VAP™ Solvent Evaporation System, both commercially available from the Horizon Technology Company, using EPA Method 1664A. The corn oil removed from the ground corn product can be greater than 0.6 wt %, greater than 0.7 wt %, or greater than 0.75 wt % to about 0.9 wt %, about 1 wt %, about 1.2 wt %, or greater of the total weight of the ground corn product. For example, the corn oil removed from the ground corn product can be greater than 0.6 wt % to about 1.2 wt %, greater than 0.65 wt % to about 1.1 wt %, or greater than 0.7 wt % to about 1.05 wt % of the total weight of the ground corn product. In some examples, the amount of corn oil that can be separated from the ground corn product can be greater than 0.6 wt %, greater than 0.7 wt %, or greater than 0.75 wt % to about 0.9 wt %, about 1 wt %, about 1.2 wt %, or greater of the total weight of the ground corn product. In another example, the corn oil removed from the ground corn product, e.g., the stillage, can be greater than 0.6 wt %, greater than 0.7 wt %, greater than 0.75 wt %, greater than 0.8 wt %, or greater than 0.85 wt % to about 0.9 wt %, about 1 wt %, about 1.2 wt %, about 1.3 wt %, about 1.4 wt %, about 1.5 wt %, about 1.6 wt %, about 1.7 wt %, about 1.8 wt %, about 1.9 wt %, about 2 wt %, about 2.3 wt %, about 2.5 wt %, about 2.7 wt %, about 3 wt %, about 3.3 wt %, about 3.5 wt %, about 3.7 wt %, about 4 wt %, or greater of the total weight of the ground corn product.

EXAMPLES

In order to provide a better understanding of the foregoing discussion, the following non-limiting examples are offered. Although the examples can be directed to specific embodiments, they are not to be viewed as limiting the invention in any specific respect.

Corn Sample Grind Description

For Exs. 1-4 the following mill or mills were used as specified in each example. The hammer mill was a Model MG mill, manufactured by Kelly Duplex Mill and Manufacturing Company in Springfield, Ohio. The pulverizer was a Model 16-H air swept pulverizer manufactured by Schutz-O'Neill Company in Minneapolis, Minn. The disk mill fiberizer was a Model TOQ-18 fiberizer, manufactured by Reynolds Engineering & Equipment, Inc. in Muscatine, Iowa.

Ex. 1 was corn that was passed through the hammer mill and through the air swept pulverizer. Raw whole corn kernels were milled to produce hammermilled corn pieces. The hammer mill was operated at about 90 Hz with a tip speed of about 124 meters per second (about 24,500 fpm) using a number 8 screen (3.175 mm) or (⁸⁄₆₄", or 0.125") at a feed rate of about 925 kg/hr (about 2,040 lbs/hr). The hammermilled corn pieces were pulverized in the air swept pulverizer to produce the ground corn product. The air swept pulverizer was operated at about 80 Hz with a tip speed of about 157 meters per second (about 30,840 fpm) using three 43.18 cm (about 17-inch) diameter CCD beater plates and a CLP liner at a feed rate of about 599 kg/hr (about 1,320 lbs/hr).

Ex. 2 was the same as Ex. 1, but the speed of the air swept pulverizer was reduced as compared to the air swept pulverizer in Ex. 1. Raw whole corn kernels were milled to produce hammermilled corn pieces. The hammer mill was operated at about 90 Hz with a tip speed of about 124 meters per second (about 24,500 fpm) using a number 8 screen (3.175 mm) or (⁸⁄₆₄", or 0.125") at a feed rate of about 925 kg/hr (about 2,040 lbs/hr). The hammermilled corn pieces were pulverized in the air swept pulverizer to produce the ground corn product. The air swept pulverizer was operated at about 50 Hz with a tip speed of about 97.9 meters per second (about 19,270 fpm) using three 43.18 cm (about 17-inch) diameter CCD beater plates and a CLP liner at a feed rate of about 599 kg/hr (about 1,320 lbs/hr).

Ex. 3 was whole corn that was only run through a disk mill fiberizer. Raw whole corn kernels were milled in the disk mill fiberizer to produce the ground corn product. The disk mill fiberizer used a 45.72 cm (18-inch) diameter TQ18-016 fine tooth plates set with a gap of about 762 μm (about 0.030 inches) and was operated at about 60 Hz with a tip speed of about 124 meters per second (about 24,500 fpm) at a feed rate of about 413 kg/hr (about 910 lbs/hr).

Ex. 4 was corn that was passed through a hammer mill and a disk mill fiberizer. Raw whole corn kernels were milled to produce hammermilled corn pieces. The hammer mill was operated at about 90 Hz with a tip speed of about 124 meters per second (about 24,500 fpm) using a number 8 screen (3.175 mm) or (⁸⁄₆₄", or 0.125") at a feed rate of about 925 kg/hr (about 2,040 lbs/hr). The hammermilled corn pieces were milled in the disk mill fiberizer to produce the ground corn product. The disk mill fiberizer used 45.72 cm (about 18-inch) diameter TQ18-016 fine tooth plates set with a gap of about 2.54 mm (about 0.100 inches) and was operated at about 60 Hz with a tip speed of about 124 meters per second (about 24,500 fpm) at a feed rate of about 1,890 kg/hr (about 4,170 lbs/hr).

CEx. 1 was corn that was passed through a hammer mill. CEx. 2 was corn that was run through a quad pair set up (a stack of 4 pairs of rolls) roller mill. The corn used in Exs. 1-4 were sourced locally in Muscatine, Iowa; the corn used in CEx. 1 was sourced from a Flint Hills Resources Fairbank facility; and the corn used in CEx. 2 was sourced from RMS in Tea, S. Dak.

Particle Size and Distribution

Table 1 shows the particle size by weight of the ground corn products as measured with sieves for Exs. 1-4 and CExs. 1-2. The sieves analysis was conducted according to the AOAC Official Method 965.22 "Sorting Corn Grits—Sieving Method," available from the AOAC International. The weight percent of the sample that was left on the specified sieve size had a particle size larger than the respective sieve size. For example, in Table 1, the sample particles in Ex. 3 had the following weight percent (wt %) particles for the respective particle sizes: 0.10 wt % larger than 850 µm, 3.60 wt % larger than 425 µm to 850 µm, 4.80 wt % larger than 250 µm to 425 µm, 1.50 wt % larger than 180 µm to 250 µm, 14.90 wt % larger than 150 µm to 180 µm, 9.75 wt % larger than 105 µm to 150 µm, and 65.35 wt % 105 µm or less in the pan.

TABLE 1

Particle Size by Weight (measured with sieves)

| Sieve Size (µm) | Particle Size (µm) | Weight Percent Left on Sieve (wt %) | | | | | |
|---|---|---|---|---|---|---|---|
| | | Ex. 1 | Ex. 2 | Ex. 3 | Ex. 4 | CEx. 1 | CEx. 2 |
| 850 | >850 | 0.05 | 0.05 | 0.10 | 0.60 | 15.00 | 3.01 |
| 425 | >425 to 850 | 0.05 | 5.20 | 3.60 | 12.40 | 25.05 | 27.28 |
| 250 | >250 to 425 | 2.10 | 14.05 | 4.80 | 15.40 | 11.90 | 38.45 |
| 180 | >180 to 250 | 1.20 | 24.55 | 1.50 | 9.10 | 6.30 | 10.40 |
| 150 | >150 to 180 | 21.90 | 15.55 | 14.90 | 4.80 | 3.90 | 9.13 |
| 105 | >105 to 150 | 15.00 | 8.85 | 9.75 | 16.25 | 7.90 | 6.72 |
| pan | 105 and smaller | 59.70 | 31.75 | 65.35 | 41.25 | 29.95 | 5.02 |

Table 2 shows the particle size by volume of the ground corn products and Table 3 shows the particle size distribution by volume of the ground corn products that were analyzed on a LS™ 13-320 laser diffraction particle size analyzer with a Tornado dry sample module attachment, both commercially available from Beckman Coulter Life Sciences. The laser diffraction particle analysis was conducted according to the ISO 13320:2009 "Particle Size Analysis—Laser Diffraction Methods".

The particle size by volume of the ground corn products shown in Table 2 is smaller than the particle size listed. For example: 10 vol % of the particles in the Ex. 3 sample had a particle size smaller than 17.68 µm.

TABLE 2

Particle Size by Volume (measured by laser diffraction)

| vol % | Particle Size (µm) | | | | | |
|---|---|---|---|---|---|---|
| | Ex. 1 | Ex. 2 | Ex. 3 | Ex. 4 | CEx. 1 | CEx. 2 |
| 10 | 18.34 | 24.92 | 17.68 | 21.10 | 88.71 | 135.20 |
| 25 | 54.89 | 101.10 | 47.44 | 92.33 | 282.90 | 304.80 |
| 50 | 168.70 | 287.90 | 167.10 | 285.00 | 686.50 | 531.60 |
| 75 | 404.20 | 630.30 | 486.70 | 587.40 | 1111.00 | 797.10 |
| 90 | 793.30 | 1097.00 | 967.70 | 876.20 | 1450.00 | 1125.00 |

Table 3 gives the complete distribution of particles within each of the listed size ranges. For example: 28.3 vol % of the particles in the Ex. 3 sample had a particle size of greater than 4 µm (e.g., about 4.01 µm) to about 60 µm.

TABLE 3

Volume % by Particle Size

| Particle Size (µm) | Particle Size Distribution (vol %) | | | | | |
|---|---|---|---|---|---|---|
| | Ex. 1 | Ex. 2 | Ex. 3 | Ex. 4 | CEx. 1 | CEx. 2 |
| 0-4 | 0 | 0 | 0 | 0 | 0 | 0 |
| >4-60 | 26.3 | 25.1 | 28.3 | 19.6 | 7.8 | 4.9 |
| >60-400 | 48.5 | 49.5 | 42.5 | 40.2 | 23.9 | 29.8 |
| >400-800 | 15.4 | 20.8 | 15.4 | 27.2 | 25.6 | 40.5 |
| >800-2,000 | 9.9 | 4.6 | 13.9 | 13.0 | 42.7 | 24.8 |

Oil and Grease Analysis

Each liquefaction sample was first centrifuged to separate the slurry into separate phases. Each phase was subjected to oil and grease analysis. Oil and grease testing was performed on the SPE-DEX® 3000XL Automated Extractor System and the SPEED-VAP™ Solvent Evaporation System, both commercially available from the Horizon Technology Company. The Horizon Technology automated extraction method, EPA Method 1664A, has been modified and validated to only remove liberated oil from the sample, leaving any oil that may be bound by the corn cellular matrix. The total average weight percent values are listed as the average of two analysis, summarized in Table 4.

TABLE 4

| Sample | Percent recoveries of each slurry sample level after separation by centrifuge and their averages Total average oil/grease (wt %) |
|---|---|
| Ex. 1 | 0.97 |
| Ex. 2 | 1.01 |
| Ex. 3 | 1.03 |
| Ex. 4 | 0.70 |
| CEx. 1 | 0.26 |
| CEx. 2 | 0.55 |

As shown in Table 4, the average amount of oil/grease recovered in Examples 1-4 was significantly greater than the amount of oil/grease recovered in the Comparative Examples 1 and 2.

Microscopy Analysis

On each selected dry ground sample, microscopy was performed using polarized light and iodine staining on both a Wild Heerbrugg Observation microscope (10×) and an AmScope trinocular microscope (50×-500×). Observation for starch and fiber were noted.

Analytical Methodology

Liquefaction

About 70 g of each ground corn sample was combined with about 200 mL of water having a temperature of about 80° C. to provide a slurry of about 35 wt % of ground corn. About 1 mL of alpha amylase was added to the slurry. Enough 1.2 M HCl was added to each slurry to adjust the pH of the slurry to about 4. Each slurry sample was then placed in a shaker water bath at about 85° C. for about 60 min. After removing slurry sample from the shaker bath, about 0.3 mL of 12 M HCl was added to lower the slurry pH and arrest the amylase activity. The time needed to complete each process of liquefaction for each sample slurry was kept constant to limit sample to sample variability.

Oil and Grease Analysis

About 2 g of each ground corn sample and about 100 mL of diluted distilled water were combined in a vial. Drops of HCl was added to the diluted sample in the vial until the pH of sample was adjusted to less than 2. Oil and grease extraction and testing was performed on the SPE-DEX® 3000XL Automated Extractor System and the SPEED-VAP™ Solvent Evaporation System, both commercially available from the Horizon Technology Company. The sample was processed by the extractor and evaporation systems using hexane as the extraction solvent. The results for the oil and grease analysis are reported in Table 4.

Microscopy Analysis

For Comparative Examples 1-2 and Examples 1-4, microscopy was performed using polarized light and iodine staining on both a Wild Heerbrugg observation microscope having a magnification of 10× (FIGS. 1, 3, 5, 7, 9, and 11) and an AmScope trinocular microscope that had a magnification of 50×-500× (FIGS. 2, 4, 6, 8, 10, and 12).

Iodine Staining Procedure

About 1 g of each ground corn sample was combined with 14 mL distilled water in a 250 mL beaker. About 1 mL of pH 5 buffer was added to the solution. About 84 mL of distilled water was combined with about 1.2 mL of a 0.5 N iodine solution and added to the sample slurry. One or two drops of the sample was transferred to a slide and blended with about 1-2 drops of an aqueous glycerin solution (about 50 wt % of glycerin and about 50 wt % of water). A cover slip was placed on the sample and the sample was observed under the microscope at the referenced magnifications. In the iodine stained sample under polarized light, a distinct Maltese cross formed in each of the starch particles. Particles of fiber and other material appeared brown or showed no color on a lightly blue hued background.

In the CEx. 1 sample of hammer milled corn, pericarp and floury endosperm particles were viewed at 10× magnification (FIG. 1) and starch and fiber particles were viewed at 200× magnification (FIG. 2).

Figures 3, 4:
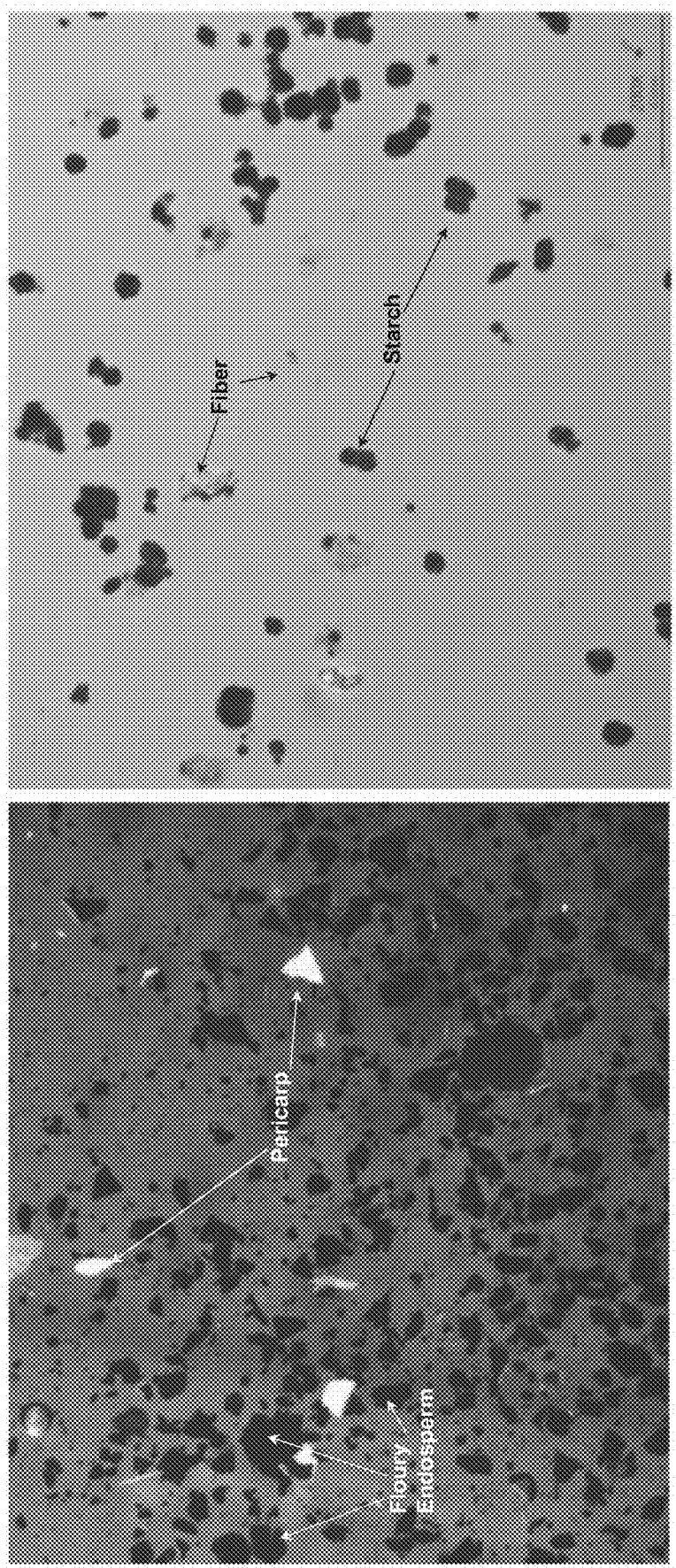
FIG. 3 is an optical microscope image of roller milled corn (Comparative Example 2) at a magnification of 10×.
FIG. 4 is an optical microscope image of roller milled corn (Comparative Example 2) at a magnification of 200×.

In the CEx. 2 sample of roller milled corn, pericarp and floury endosperm particles were viewed at 10× magnification (FIG. 3) and starch and fiber particles were viewed at 200× magnification (FIG. 4).

Figure 6:
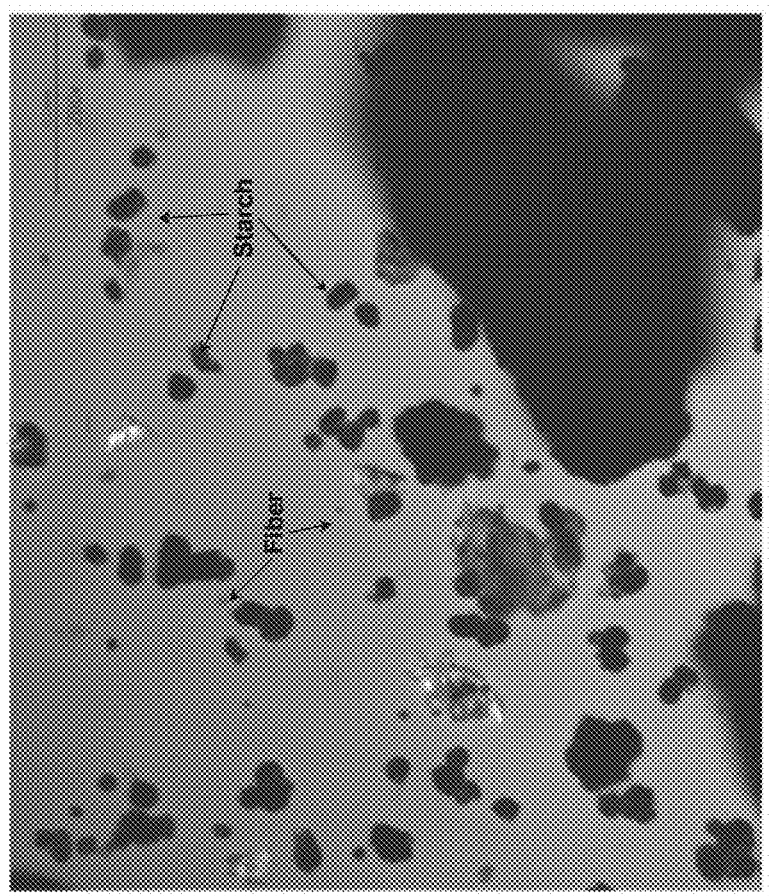
FIG. 6 is an optical microscope image of disk pulverized corn (Example 1) at a magnification of 200×.
Figure 5:
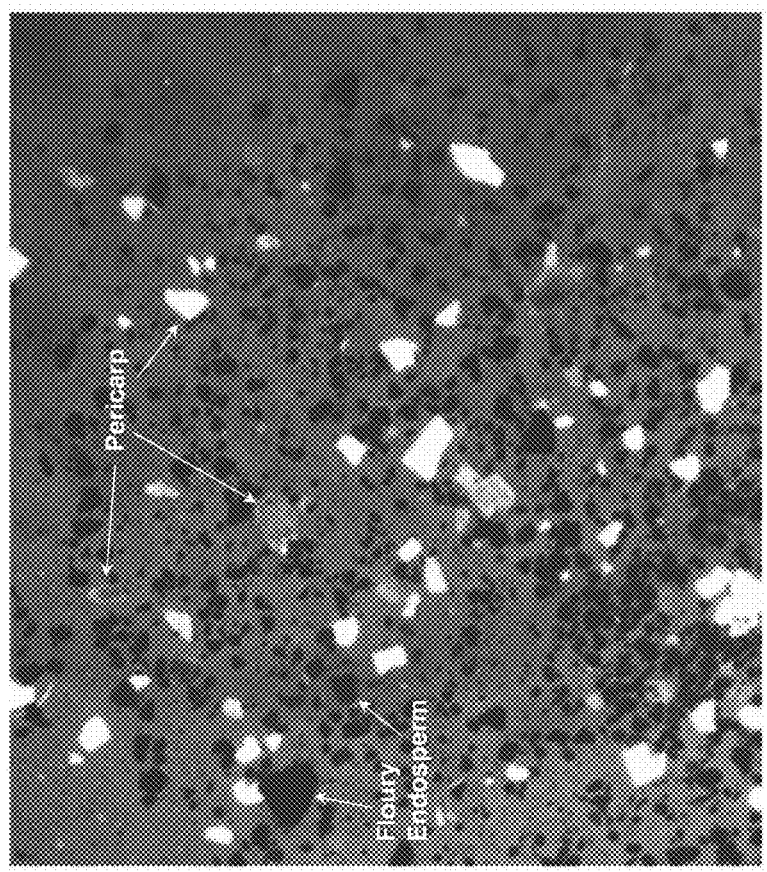
FIG. 5 is an optical microscope image of disk pulverized corn (Example 1) at a magnification of 10×.

In the Ex. 1 sample of disk pulverized corn, pericarp and floury endosperm particles were viewed at 10× magnification (FIG. 5) and starch and fiber particles were viewed at 200× magnification (FIG. 6).

Figure 8:
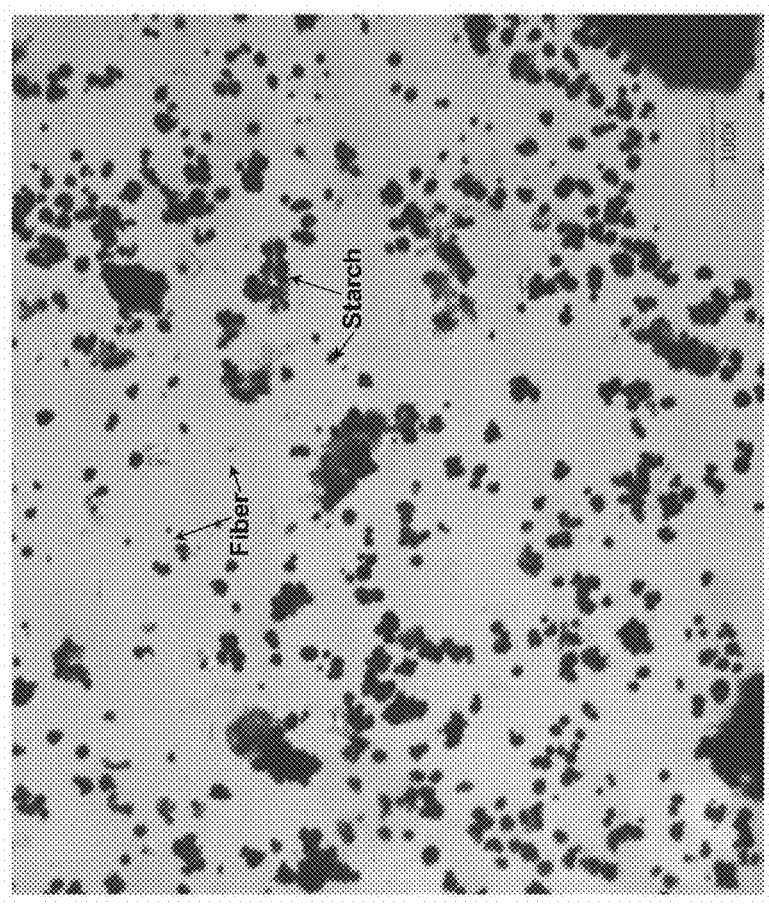
FIG. 8 is an optical microscope image of disk pulverized corn (Example 2) at a magnification of 100×.
Figure 7:
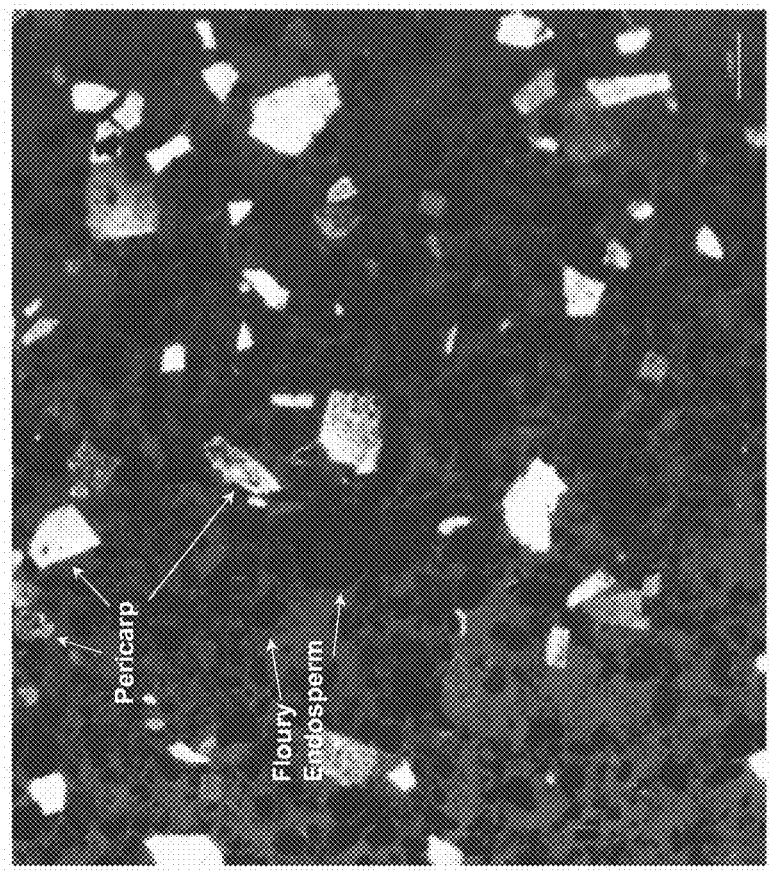
FIG. 7 is an optical microscope image of disk pulverized corn (Example 2) at a magnification of 10×.

In the Ex. 2 sample of disk pulverized corn, pericarp and floury endosperm particles were viewed at 10× magnification (FIG. 7) and starch and fiber particles were viewed at 100× magnification (FIG. 8).

Figure 10:
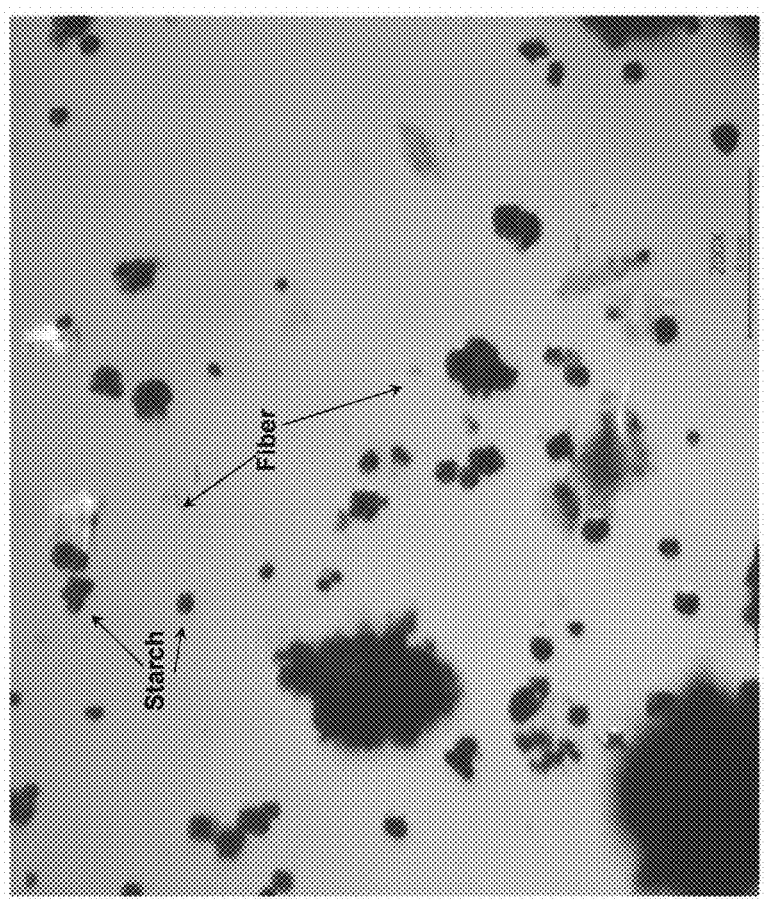
FIG. 10 is an optical microscope image of disk fiberized corn (Example 3) at a magnification of 200×.
Figure 9:
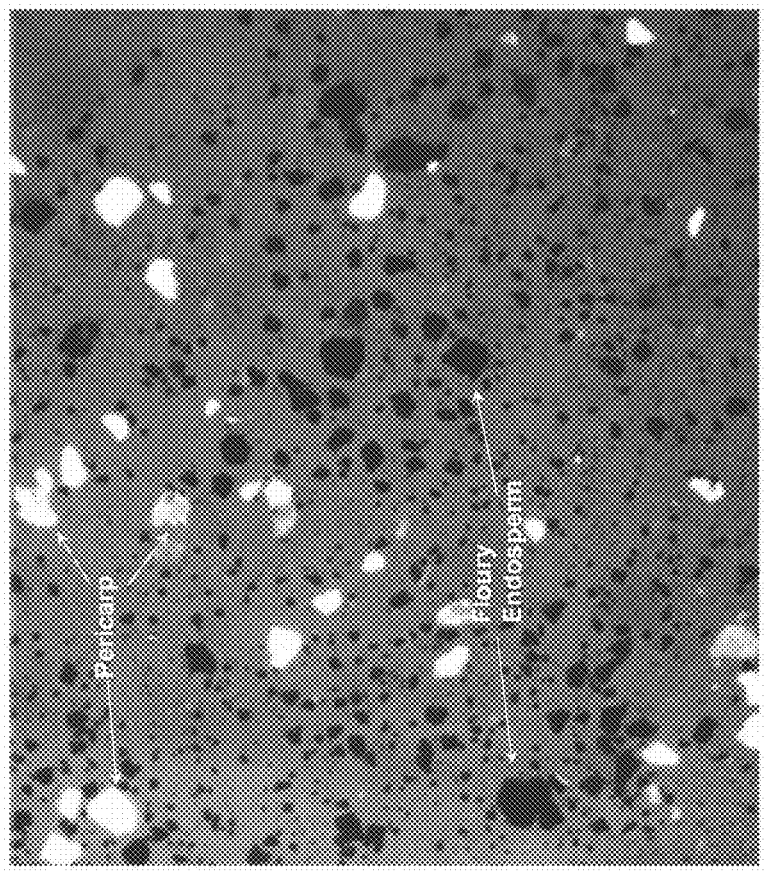
FIG. 9 is an optical microscope image of disk fiberized corn (Example 3) at a magnification of 10×.

In the Ex. 3 sample of disk fiberized corn, pericarp and floury endosperm particles were viewed at 10× magnification (FIG. 9) and starch and fiber particles were viewed at 200× magnification (FIG. 10).

Figures 11, 12:
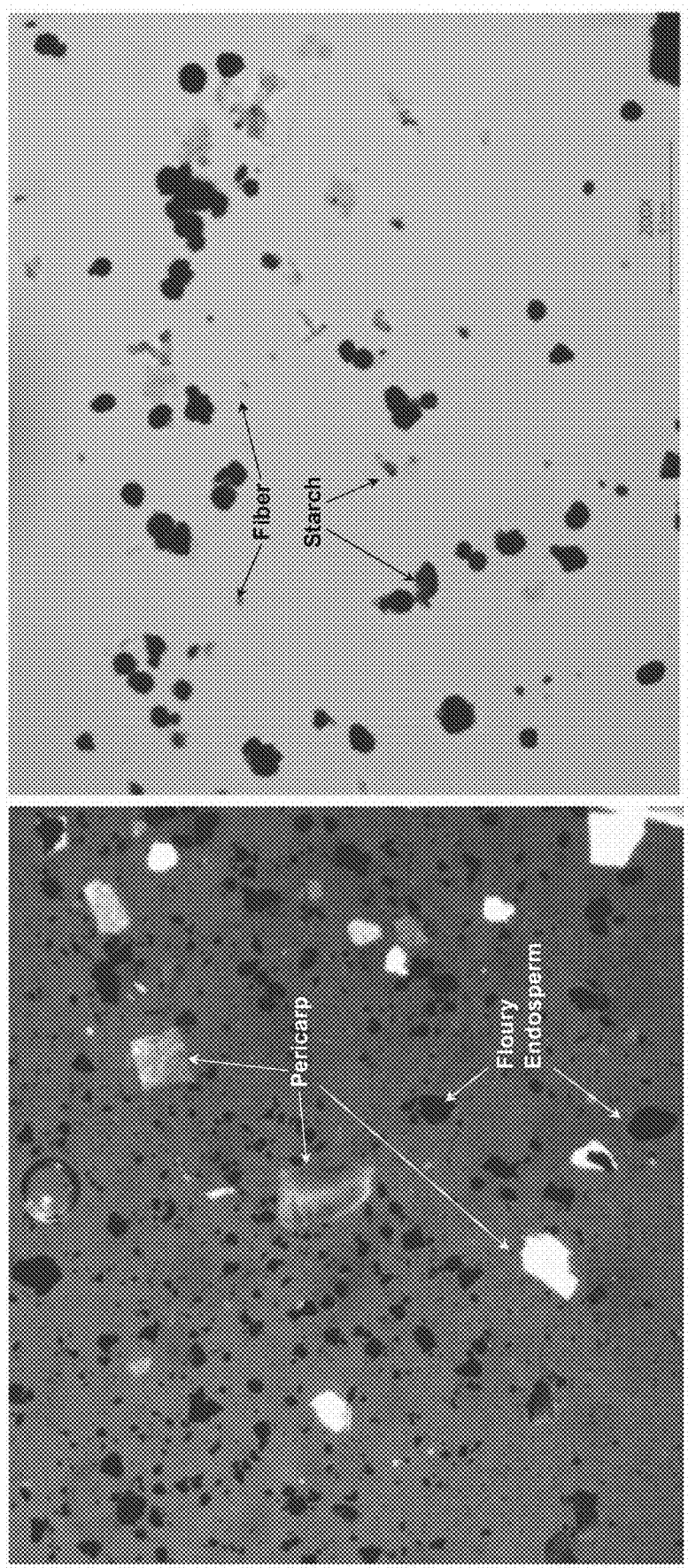
FIG. 11 is an optical microscope image of disk fiberized corn (Example 4) at a magnification of 10×.
FIG. 12 is an optical microscope image of disk fiberized corn (Example 4) at a magnification of 200×.

In the Ex. 4 sample of disk fiberized corn, pericarp and floury endosperm particles were viewed at 10× magnification (FIG. 11) and starch and fiber particles were viewed at 200× magnification (FIG. 12).

Embodiments of the present disclosure further relate to any one or more of the following paragraphs:

1. A method for producing ethanol, comprising: introducing a plurality of corn pieces into a mill, wherein the plurality of corn pieces comprises whole corn kernels, fragmented corn kernels, size-reduced corn kernels, milled corn kernels, or any mixture thereof; milling the corn pieces in the mill to produce a ground corn product, wherein greater than 25 wt % of the ground corn product has a particle size of greater than 105 µm, and wherein greater than 80 wt % of the ground corn product has a particle size of 425 µm or less, as measured according to AOAC 965.22-1966; processing the ground corn product to produce a fermentation mash comprising ethanol; and removing the ethanol from the fermentation mash to produce a stillage.

2. A method for producing ethanol, comprising: introducing a plurality of corn pieces into a mill, wherein the plurality of corn pieces comprises whole corn kernels, fragmented corn kernels, size-reduced corn kernels, milled corn kernels, or any mixture thereof; milling the corn pieces in the mill to produce a ground corn product, wherein the ground corn product has a $d_{50}$ by volume percent of 100 µm to 400 µm, as measured according to ISO 13320:2009; processing the ground corn product to produce a fermentation mash comprising ethanol; and removing the ethanol from the fermentation mash to produce a stillage.

3. A method for producing ethanol, comprising: introducing a plurality of corn pieces into a mill, wherein the plurality of corn pieces comprises whole corn kernels, fragmented corn kernels, size-reduced corn kernels, milled corn kernels, or any mixture thereof; milling the corn pieces in the mill to produce a ground corn product, wherein a plurality of total particles of the ground corn product comprises a plurality of fiber particles, and wherein the fiber particles of the ground corn product has a $d_{50}$ by volume percent of greater than 200 µm and the total particles of the ground corn product has a $d_{50}$ by volume percent of less than 500 µm, as measured according to ISO 13320:2009; processing the ground corn product to produce a fermentation mash comprising ethanol; and removing the ethanol from the fermentation mash to produce a stillage.

4. A method for producing ethanol, comprising: introducing a plurality of corn pieces into a mill, wherein the plurality of corn pieces comprises whole corn kernels, fragmented corn kernels, size-reduced corn kernels, milled corn kernels, or any mixture thereof; milling the corn pieces in the mill to produce a ground corn product, wherein greater than 85 wt % of the ground corn product has a particle size of 425 µm or less, as measured according to AOAC 965.22-1966, and wherein the ground corn product has a crystallinity of greater than 75%, as compared to a crystallinity of the corn pieces; processing the ground corn product to produce a fermentation mash comprising ethanol; and removing the ethanol from the fermentation mash to produce a stillage.

5. A method for producing ethanol, comprising: introducing a plurality of corn pieces into a mill, wherein the plurality of corn pieces comprises whole corn kernels, fragmented corn kernels, size-reduced corn kernels, milled corn kernels, or any mixture thereof, wherein the mill comprises a first rotatable disk and either a second rotatable disk or a stationary surface, and wherein a distance separating the first rotatable disk and either the second rotatable disk or the stationary surface provides a shearing gap therebetween; rotating at least the first rotatable disk and having the shearing gap located between the first rotatable disk and either the second rotatable disk or the stationary surface during rotation of at least the first rotatable disk; contacting the corn pieces to and shearing the corn pieces between the first rotatable disk and either the second rotatable disk or the stationary surface in the shearing gap to produce a ground corn product, wherein greater than 25 wt % of the ground corn product has a particle size of greater than 105 µm, and wherein greater than 80 wt % of the ground corn product has a particle size of 425 µm or less, as measured according to AOAC 965.22-1966; processing the ground corn product to produce a fermentation mash comprising ethanol; and removing the ethanol from the fermentation mash to produce a stillage.

6. A method for producing ethanol, comprising: introducing a plurality of corn pieces into a mill, wherein the plurality of corn pieces comprises whole corn kernels, fragmented corn kernels, size-reduced corn kernels, milled corn kernels, or any mixture thereof, wherein the mill comprises a first rotatable disk and either a second rotatable disk or a stationary surface, and wherein a set of grinding teeth is disposed on the first rotatable disk, the second rotatable disk, or the stationary surface; contacting the corn pieces to and shearing the corn pieces between the first rotatable disk and either the second rotatable disk or the stationary surface to produce a ground corn product, wherein greater than 25 wt % of the ground corn product has a particle size of greater than 105 μm, and wherein greater than 80 wt % of the ground corn product has a particle size of 425 μm or less, as measured according to AOAC 965.22-1966; processing the ground corn product to produce a fermentation mash comprising ethanol; and removing the ethanol from the fermentation mash to produce a stillage.

7. A method for producing ethanol, comprising: introducing a plurality of corn pieces into a mill, wherein the plurality of corn pieces comprises whole corn kernels, fragmented corn kernels, size-reduced corn kernels, milled corn kernels, or any mixture thereof, wherein the mill comprises a first set of grinding teeth disposed on a first rotatable disk and a second set of grinding teeth disposed on either a second rotatable disk or a stationary surface, and wherein a distance separating the first set of grinding teeth and the second set of grinding teeth provides a shearing gap therebetween; contacting the corn pieces to the first set of grinding teeth and the second set of grinding teeth, wherein at least the first set of grinding teeth is rotating with the first rotatable disk; shearing the corn pieces between the first set of grinding teeth and the second set of grinding teeth in the shearing gap to produce a ground corn product; processing the ground corn product to produce a fermentation mash comprising ethanol; and removing the ethanol from the fermentation mash to produce a stillage.

8. A method for producing ethanol, comprising: introducing a plurality of corn pieces into a mill, wherein the plurality of corn pieces comprises whole corn kernels, fragmented corn kernels, size-reduced corn kernels, milled corn kernels, or any mixture thereof, wherein the mill comprises a first set of grinding teeth disposed on a first rotatable disk and a second set of grinding teeth disposed on either a second rotatable disk or a stationary surface, and wherein a distance separating the first set of grinding teeth and the second set of grinding teeth provides a shearing gap therebetween; contacting the corn pieces to the first set of grinding teeth and the second set of grinding teeth, wherein at least the first set of grinding teeth is rotating with the first rotatable disk; shearing the corn pieces between the first set of grinding teeth and the second set of grinding teeth in the shearing gap to produce a ground corn product, wherein greater than 85 wt % of the ground corn product has a particle size of 425 μm or less, as measured according to AOAC 965.22-1966, and wherein the ground corn product has a crystallinity of greater than 75%, as compared to a crystallinity of the unground corn kernels; processing the ground corn product to produce a fermentation mash comprising ethanol; and removing the ethanol from the fermentation mash to produce a stillage.

9. A ground corn product, comprising ground corn kernels, wherein greater than 85 wt % of the ground corn product has a particle size of 425 μm or less, as measured according to AOAC 965.22-1966, and wherein the ground corn product has a crystallinity of greater than 75%, as compared to a crystallinity of the unground corn kernels.

10. A ground corn product, comprising ground corn kernels, wherein the ground corn product has a $d_{50}$ of by volume percent of 100 μm to 400 μm, as measured according to ISO 13320:2009.

11. A ground corn product, comprising ground corn kernels, wherein a plurality of total particles of the ground corn product comprises a plurality of fiber particles, and wherein the fiber particles of the ground corn product has a $d_{50}$ by volume percent of greater than 200 μm and the total particles of the ground corn product has a $d_{50}$ by volume percent of less than 500 μm, as measured according to ISO 13320:2009.

12. A ground corn product, comprising ground corn kernels, wherein greater than 25 wt % of the ground corn product has a particle size of greater than 105 μm, and wherein greater than 80 wt % of the ground corn product has a particle size of 425 μm or less, as measured according to AOAC 965.22-1966.

13. The method according to any one of paragraphs 1-8, further comprising removing corn oil from the ground corn product, wherein the corn oil removed from the ground corn product is greater than 0.6 wt % of a total weight of the ground corn product.

14. The method or the ground corn product according to any one of paragraphs 1-3, 5-8, and 10-12, wherein the ground corn product has a crystallinity of greater than 75%, as compared to a crystallinity of the corn pieces.

15. The method or the ground corn product according to any one of paragraphs 1 to 14, wherein the ground corn product has a crystallinity of greater than 85%, as compared to a crystallinity of the corn pieces.

16. The method or the ground corn product according to any one of paragraphs 1 to 15, wherein the ground corn product has a crystallinity of greater than 90%, as compared to a crystallinity of the corn pieces.

17. The method or the ground corn product according to any one of paragraphs 1 to 16, wherein the ground corn product has a crystallinity of greater than 95%, as compared to a crystallinity of the corn pieces.

18. The method or the ground corn product according to any one of paragraphs 1 to 17, wherein the ground corn product has a crystallinity of greater than 99%, as compared to a crystallinity of the corn pieces.

19. The method or the ground corn product according to any one of paragraphs 1 to 18, wherein the ground corn product has a $d_{10}$ by volume percent of 10 μm to 30 μm, as measured according to ISO 13320:2009.

20. The method or the ground corn product according to any one of paragraphs 1 to 19, wherein the ground corn product has a $d_{10}$ by volume percent of 15 μm to 25 μm, as measured according to ISO 13320:2009.

21. The method or the ground corn product according to any one of paragraphs 1, 3-9, 11, and 12, wherein the ground corn product has a $d_{50}$ by volume percent of 100 μm to 500 μm, as measured according to ISO 13320:2009.

22. The method or the ground corn product according to any one of paragraphs 1, 3-9, 11, and 12, wherein the ground corn product has a $d_{50}$ by volume percent of 125 μm to 400 μm, as measured according to ISO 13320:2009.

23. The method or the ground corn product according to any one of paragraphs 1 to 22, wherein the ground corn product has a $d_{50}$ by volume percent of 150 μm to 300 μm, as measured according to ISO 13320:2009.

24. The method or the ground corn product according to any one of paragraphs 1 to 23, wherein the ground corn product has a $d_{90}$ by volume percent of 700 μm to 1,100 μm, as measured according to ISO 13320:2009.

25. The method or the ground corn product according to any one of paragraphs 1 to 24, wherein the ground corn product has a $d_{90}$ by volume percent of 750 μm to 1,100 μm, as measured according to ISO 13320:2009.

26. The method or the ground corn product according to any one of paragraphs 1 to 25, wherein the ground corn product has a $d_{90}$ by volume percent of 800 μm to 1,100 μm, as measured according to ISO 13320:2009.

27. The method or the ground corn product according to any one of paragraphs 1 to 26, wherein greater than 70 wt % of the ground corn product has a particle size of 250 μm or less, as measured according to AOAC 965.22-1966.

28. The method or the ground corn product according to any one of paragraphs 1 to 27, wherein greater than 50 wt % of the ground corn product has a particle size of 180 μm or less, as measured according to AOAC 965.22-1966.

29. The method or the ground corn product according to any one of paragraphs 1 to 28, wherein greater than 50 wt % of the ground corn product has a particle size of 150 μm or less, as measured according to AOAC 965.22-1966.

30. The method or the ground corn product according to any one of paragraphs 2-4, 7, and 10-12, wherein greater than 25 wt % of the ground corn product has a particle size of greater than 105 μm, and wherein greater than 80 wt % of the ground corn product has a particle size of 425 μm or less, as measured according to AOAC 965.22-1966.

31. The method or the ground corn product according to any one of paragraphs 1 to 30, wherein greater than 25 wt % of the ground corn product has a particle size of greater than 105 μm, and wherein greater than 90 wt % of the ground corn product has a particle size of 425 μm or less, as measured according to AOAC 965.22-1966.

32. The method or the ground corn product according to any one of paragraphs 1 to 31, wherein greater than 25 wt % of the ground corn product has a particle size of greater than 105 μm, and wherein greater than 60 wt % of the ground corn product has a particle size of 250 μm or less, as measured according to AOAC 965.22-1966.

33. The method or the ground corn product according to any one of paragraphs 1 to 32, wherein greater than 25 wt % of the ground corn product has a particle size of greater than 105 μm, and wherein greater than 70 wt % of the ground corn product has a particle size of 250 μm or less, as measured according to AOAC 965.22-1966.

34. The method or the ground corn product according to any one of paragraphs 1 to 33, wherein greater than 25 wt % of the ground corn product has a particle size of greater than 105 μm, and wherein greater than 50 wt % of the ground corn product has a particle size of 180 μm or less, as measured according to AOAC 965.22-1966.

35. The method or the ground corn product according to any one of paragraphs 1 to 34, wherein greater than 25 wt % of the ground corn product has a particle size of greater than 105 μm, and wherein greater than 60 wt % of the ground corn product has a particle size of 180 μm or less, as measured according to AOAC 965.22-1966.

36. The method or the ground corn product according to any one of paragraphs 1 to 35, wherein greater than 25 wt % of the ground corn product has a particle size of greater than 105 μm, and wherein greater than 70 wt % of the ground corn product has a particle size of 180 μm or less, as measured according to AOAC 965.22-1966.

37. The method or the ground corn product according to any one of paragraphs 1 to 36, wherein greater than 90 wt % of the ground corn product has a particle size of 425 μm or less, as measured according to AOAC 965.22-1966.

38. The method or the ground corn product according to any one of paragraphs 1 to 37, wherein greater than 95 wt % of the ground corn product has a particle size of 425 μm or less, as measured according to AOAC 965.22-1966.

39. The method or the ground corn product according to any one of paragraphs 1 to 38, wherein greater than 80 wt % of the ground corn product has a particle size of 250 μm or less, as measured according to AOAC 965.22-1966.

40. The method or the ground corn product according to any one of paragraphs 1 to 39, wherein greater than 90 wt % of the ground corn product has a particle size of 250 μm or less, as measured according to AOAC 965.22-1966.

41. The method or the ground corn product according to any one of paragraphs 1 to 40, wherein greater than 95 wt % of the ground corn product has a particle size of 250 μm or less, as measured according to AOAC 965.22-1966.

42. The method or the ground corn product according to any one of paragraphs 1 to 41, wherein greater than 60 wt % of the ground corn product has a particle size of 180 μm or less, as measured according to AOAC 965.22-1966.

43. The method or the ground corn product according to any one of paragraphs 1 to 42, wherein greater than 70 wt % of the ground corn product has a particle size of 180 μm or less, as measured according to AOAC 965.22-1966.

44. The method or the ground corn product according to any one of paragraphs 1 to 43, wherein greater than 80 wt % of the ground corn product has a particle size of 180 μm or less, as measured according to AOAC 965.22-1966.

45. The method or the ground corn product according to any one of paragraphs 1 to 44, wherein greater than 90 wt % of the ground corn product has a particle size of 180 μm or less, as measured according to AOAC 965.22-1966.

46. The method or the ground corn product according to any one of paragraphs 1 to 45, wherein greater than 50 wt % of the ground corn product has a particle size of 150 μm or less, as measured according to AOAC 965.22-1966.

47. The method or the ground corn product according to any one of paragraphs 1 to 46, wherein greater than 60 wt % of the ground corn product has a particle size of 150 μm or less, as measured according to AOAC 965.22-1966.

48. The method or the ground corn product according to any one of paragraphs 1 to 47, wherein greater than 70 wt % of the ground corn product has a particle size of 150 μm or less, as measured according to AOAC 965.22-1966.

49. The method or the ground corn product according to any one of paragraphs 1 to 48, wherein greater than 90 wt % of the ground corn product has a particle size of 425 μm or less, and wherein greater than 80 wt % of the ground corn product has a particle size of 250 μm or less, as measured according to AOAC 965.22-1966.

50. The method or the ground corn product according to any one of paragraphs 1 to 49, wherein greater than 90 wt % of the ground corn product has a particle size of 250 μm or less, and wherein greater than 70 wt % of the ground corn product has a particle size of 180 μm or less, as measured according to AOAC 965.22-1966.

51. The method or the ground corn product according to any one of paragraphs 1 to 50 the preceding paragraphs, wherein greater than 90 wt % of the ground corn product has a particle size of 250 μm or less, and wherein greater than 60 wt % of the ground corn product has a particle size of 150 μm or less, as measured according to AOAC 965.22-1966.

52. The method or the ground corn product according to any one of paragraphs 1 to 51, wherein about 10 vol % of the ground corn product has a particle size of 25 μm or less, as measured according to ISO 13320:2009.

53. The method or the ground corn product according to any one of paragraphs 1 to 52, wherein greater than 2 vol % of the ground corn product has a particle size of 25 μm or less, as measured according to ISO 13320:2009.

54. The method or the ground corn product according to any one of paragraphs 1 to 53, wherein greater than 5 vol % of the ground corn product has a particle size of 25 μm or less, as measured according to ISO 13320:2009.

55. The method or the ground corn product according to any one of paragraphs 1 to 54, wherein greater than 15 vol % of the ground corn product has a particle size of 60 μm or less, as measured according to ISO 13320:2009.

56. The method or the ground corn product according to any one of paragraphs 1 to 55, wherein greater than 18 vol % of the ground corn product has a particle size of 60 μm or less, as measured according to ISO 13320:2009.

57. The method or the ground corn product according to any one of paragraphs 1 to 56, wherein greater than 20 vol % of the ground corn product has a particle size of 60 μm or less, as measured according to ISO 13320:2009.

58. The method or the ground corn product according to any one of paragraphs 1 to 57, wherein greater than 25 vol % of the ground corn product has a particle size of 60 μm or less, as measured according to ISO 13320:2009.

59. The method or the ground corn product according to any one of paragraphs 1 to 58, wherein greater than 40 vol % of the ground corn product has a particle size of 400 μm or less, as measured according to ISO 13320:2009.

60. The method or the ground corn product according to any one of paragraphs 1 to 59, wherein greater than 50 vol % of the ground corn product has a particle size of 400 μm or less, as measured according to ISO 13320:2009.

61. The method or the ground corn product according to any one of paragraphs 1 to 60, wherein greater than 55 vol % of the ground corn product has a particle size of 400 μm or less, as measured according to ISO 13320:2009.

62. The method or the ground corn product according to any one of paragraphs 1 to 61, wherein greater than 60 vol % of the ground corn product has a particle size of 400 μm or less, as measured according to ISO 13320:2009.

63. The method or the ground corn product according to any one of paragraphs 1 to 62, wherein greater than 70 vol % of the ground corn product has a particle size of 400 μm or less, as measured according to ISO 13320:2009.

64. The method or the ground corn product according to any one of paragraphs 1 to 63, wherein greater than 80 vol % of the ground corn product has a particle size of 800 μm or less, as measured according to ISO 13320:2009.

65. The method or the ground corn product according to any one of paragraphs 1 to 64, wherein greater than 85 vol % of the ground corn product has a particle size of 800 μm or less, as measured according to ISO 13320:2009.

66. The method or the ground corn product according to any one of paragraphs 1 to 65, wherein greater than 90 vol % of the ground corn product has a particle size of 800 μm or less, as measured according to ISO 13320:2009.

67. The method or the ground corn product according to any one of paragraphs 1 to 66, wherein greater than 95 vol % of the ground corn product has a particle size of 800 μm or less, as measured according to ISO 13320:2009.

68. The method or the ground corn product according to any one of paragraphs 1 to 67, wherein greater than 18 vol % of the ground corn product has a particle size of 60 μm or less, and wherein greater than 50 vol % of the ground corn product has a particle size of 400 μm or less, as measured according to ISO 13320:2009.

69. The method or the ground corn product according to any one of paragraphs 1 to 68, wherein greater than 20 vol % of the ground corn product has a particle size of 60 μm or less, and wherein greater than 60 vol % of the ground corn product has a particle size of 400 μm or less, as measured according to ISO 13320:2009.

70. The method or the ground corn product according to any one of paragraphs 1 to 69, wherein greater than 18 vol % of the ground corn product has a particle size of 60 μm or less, and wherein greater than 85 vol % of the ground corn product has a particle size of 800 μm or less, as measured according to ISO 13320:2009.

71. The method or the ground corn product according to any one of paragraphs 1 to 70, wherein greater than 50 vol % of the ground corn product has a particle size of 400 μm or less, and wherein greater than 85 vol % of the ground corn product has a particle size of 800 μm or less, as measured according to ISO 13320:2009.

72. The method or the ground corn product according to any one of paragraphs 1 to 71, wherein greater than 22 vol % of the ground corn product has a particle size of 60 μm or less, wherein greater than 60 vol % of the ground corn product has a particle size of 400 μm or less, and wherein greater than 90 vol % of the ground corn product has a particle size of 800 μm or less, as measured according to ISO 13320:2009.

73. The method or the ground corn product according to any one of paragraphs 1 to 72, wherein a plurality of total particles of the ground corn product comprises a plurality of fiber particles, and wherein the fiber particles of the ground corn product has a $d_{50}$ by volume percent of 125 μm to 450 μm and the total particles of the ground corn product has a $d_{50}$ by volume percent of 100 μm to 400 μm, as measured according to ISO 13320:2009.

74. The method or the ground corn product according to any one of paragraphs 1 to 73, wherein a plurality of total particles of the ground corn product comprises a plurality of fiber particles, and wherein the fiber particles of the ground corn product has a $d_{50}$ by volume percent of 150 μm to 400 μm and the total particles of the ground corn product has a $d_{50}$ by volume percent of 125 μm to 300 μm, as measured according to ISO 13320:2009.

75. The method or the ground corn product according to any one of paragraphs 1 to 74, wherein a plurality of total particles of the ground corn product comprises a plurality of fiber particles, and wherein the fiber particles of the ground corn product has a $d_{75}$ by volume percent of 375 μm to 700 μm and the total particles of the ground corn product has a $d_{75}$ by volume percent of 350 μm to 600 μm, as measured according to ISO 13320:2009.

76. The method or the ground corn product according to any one of paragraphs 1 to 75, wherein a plurality of total particles of the ground corn product comprises a plurality of fiber particles, and wherein the fiber particles of the ground corn product has a $d_{75}$ by volume percent of 400 μm to 600 μm and the total particles of the ground corn product has a $d_{75}$ by volume percent of 350 μm to 550 μm, as measured according to ISO 13320:2009.

77. The method or the ground corn product according to any one of paragraphs 1 to 76, wherein a plurality of total particles of the ground corn product comprises a plurality of fiber particles, and wherein the fiber particles of the ground corn product has a $d_{50}$ by volume percent of greater than 250 μm and the total particles of the ground corn product has a $d_{50}$ by volume percent of less than 450 µm, as measured according to ISO 13320:2009.

78. The method or the ground corn product according to any one of paragraphs 1 to 77, wherein a plurality of total particles of the ground corn product comprises a plurality of fiber particles, and wherein the fiber particles of the ground corn product has a $d_{50}$ by volume percent of greater than 300 µm and the total particles of the ground corn product has a $d_{50}$ by volume percent of less than 400 µm, as measured according to ISO 13320:2009.

79. The method or the ground corn product according to any one of paragraphs 1 to 78, wherein a plurality of total particles of the ground corn product comprises a plurality of fiber particles, and wherein the fiber particles of the ground corn product has a $d_{50}$ by volume percent of greater than 350 µm and the total particles of the ground corn product has a $d_{50}$ by volume percent of less than 350 µm, as measured according to ISO 13320:2009.

80. The method or the ground corn product according to any one of paragraphs 1 to 79, wherein a plurality of total particles of the ground corn product comprises a plurality of fiber particles, and wherein the fiber particles of the ground corn product has a $d_{50}$ by volume percent of greater than 200 µm to 500 µm and the total particles of the ground corn product has a $d_{50}$ by volume percent of 100 µm to less than 500 µm, as measured according to ISO 13320:2009.

81. The method according to any one of paragraphs 1-4, wherein the mill comprises a first set of grinding teeth disposed on a first rotatable disk and a second set of grinding teeth disposed on either a second rotatable disk or a stationary surface, and wherein a distance separating the first set of grinding teeth and the second set of grinding teeth provides a shearing gap therebetween.

82. The method according to any one of paragraphs 5, 7, 8, and 81, wherein a size of the shearing gap is adjusted or maintained to produce a desired distribution of particle sizes of the ground corn product.

83. The method according to any one of paragraphs 6, 7, 8, and 81, wherein each set of grinding teeth comprises triangular teeth or rectangular teeth.

84. The method according to any one of paragraphs 5, 7, 8, and 81, wherein the ground corn product passes through the shearing gap to exit the mill.

85. The method according to any one of paragraphs 1-8, wherein processing the ground corn product to produce the fermentation mash comprises: combining the ground corn product, water, and an enzyme to produce a slurry tank mixture; heating the slurry tank mixture to produce gelatinized starch; hydrolyzing the gelatinized starch to produce a liquefaction mash; and treating the liquefaction mash by saccharification and fermentation to produce the fermentation mash.

86. The method according to any one of paragraphs 1-8, wherein the mill is an air swept pulverizer or a disk mill fiberizer.

87. A ground corn product, wherein greater than 25 wt % of the ground corn product has a particle size of greater than 105 µm, and wherein greater than 80 wt % of the ground corn product has a particle size of 425 µm or less, as measured according to AOAC 965.22-1966.

88. A ground corn product, wherein the ground corn product has a $d_{50}$ by volume percent of 100 µm to 400 µm, as measured according to ISO 13320:2009.

89. A ground corn product, wherein a plurality of total particles of the ground corn product comprises a plurality of fiber particles, and wherein the fiber particles of the ground corn product has a $d_{50}$ by volume percent of greater than 200 µm and the total particles of the ground corn product has a $d_{50}$ by volume percent of less than 500 µm, as measured according to ISO 13320:2009.

90. A ground corn product, wherein greater than 85 wt % of the ground corn product has a particle size of 425 µm or less, as measured according to AOAC 965.22-1966, and wherein the ground corn product has a crystallinity of greater than 75%, as compared to a crystallinity of the corn pieces.

91. A process for making ethanol, comprising: introducing a plurality of corn pieces into a mill, wherein the plurality of corn pieces comprises whole corn kernels, fragmented corn kernels, size-reduced corn kernels, milled corn kernels, or any mixture thereof; milling the corn pieces in the mill to produce a ground corn product, wherein greater than 25 wt % of the ground corn product has a particle size of greater than 105 µm, and wherein greater than 80 wt % of the ground corn product has a particle size of 425 µm or less, as measured according to AOAC 965.22-1966; processing the ground corn product to produce a fermentation mash comprising ethanol; and separating at least a portion of the ethanol from the fermentation mash to produce a stillage.

92. A process for making ethanol, comprising: introducing a plurality of corn pieces into a mill, wherein the plurality of corn pieces comprises whole corn kernels, fragmented corn kernels, size-reduced corn kernels, milled corn kernels, or any mixture thereof; milling the corn pieces in the mill to produce a ground corn product, wherein the ground corn product has a $d_{50}$ by volume percent of 100 µm to 400 µm, as measured according to ISO 13320:2009; processing the ground corn product to produce a fermentation mash comprising ethanol; and separating at least a portion of the ethanol from the fermentation mash to produce a stillage.

93. A process for making ethanol, comprising: introducing a plurality of corn pieces into a mill, wherein the plurality of corn pieces comprises whole corn kernels, fragmented corn kernels, size-reduced corn kernels, milled corn kernels, or any mixture thereof, wherein the mill comprises a first rotatable disk and either a second rotatable disk or a stationary surface, and wherein a distance separating the first rotatable disk and either the second rotatable disk or the stationary surface provides a shearing gap therebetween; rotating the first rotatable disk; contacting the corn pieces to and shearing the corn pieces between the first rotatable disk and either the second rotatable disk or the stationary surface in the shearing gap to produce a ground corn product, wherein greater than 25 wt % of the ground corn product has a particle size of greater than 105 µm, and wherein greater than 80 wt % of the ground corn product has a particle size of 425 µm or less, as measured according to AOAC 965.22-1966; processing the ground corn product to produce a fermentation mash comprising ethanol; and separating at least a portion of the ethanol from the fermentation mash to produce a stillage.

94. The process according to any one of paragraphs 91 to 93, further comprising separating corn oil from the stillage.

95. The ground corn product or process according to any one of paragraphs 87 to 94, wherein the ground corn product has a $d_{50}$ by volume percent of 100 µm to 400 µm, as measured according to ISO 13320:2009.

96. The ground corn product or process according to any one of paragraphs 87 to 95, wherein the ground corn product has a crystallinity of greater than 75%, as compared to a crystallinity of the plurality of corn pieces prior to milling.

97. The process according to any one of paragraphs 91 to 96, wherein the mill is an air swept pulverizer or a disk mill fiberizer.

98. The ground corn product or process according to any one of paragraphs 87 to 97, wherein greater than 85 wt % of the ground corn product has a particle size of 425 μm or less, as measured according to AOAC 965.22-1966.

99. The ground corn product or process according to any one of paragraphs 87 to 98, wherein greater than 15 vol % of the ground corn product has a particle size of 60 μm or less, as measured according to ISO 13320:2009.

100. The ground corn product or process according to any one of paragraphs 87 to 99, wherein greater than 50 vol % of the ground corn product has a particle size of 400 μm or less, as measured according to ISO 13320:2009.

101. The ground corn product or process according to any one of paragraphs 87 to 94, wherein: greater than 85 wt % of the ground corn product has a particle size of 425 μm or less, as measured according to AOAC 965.22-1966, the ground corn product has a $d_{50}$ by volume percent of 100 μm to 400 μm, as measured according to ISO 13320:2009, the ground corn product has a crystallinity of greater than 75%, as compared to a crystallinity of the plurality of corn pieces prior to milling, greater than 15 vol % of the ground corn product has a particle size of 60 μm or less, as measured according to ISO 13320:2009, and greater than 50 vol % of the ground corn product has a particle size of 400 μm or less, as measured according to ISO 13320:2009.

102. The ground corn product or process according to any one of paragraphs 87 to 101, wherein the ground corn product has a $d_{50}$ by volume percent of 120 μm to 350 μm, as measured according to ISO 13320:2009.

103. The ground corn product or process according to any one of paragraphs 87 to 102, wherein the ground corn product has a $d_{10}$ by volume percent of 5 μm to 50 μm, a $d_{25}$ by volume percent of 30 μm to 150 μm, and a $d_{50}$ by volume percent of 120 μm to 350 μm.

104. The ground corn product or process according to any one of paragraphs 87 to 103, wherein greater than 15 vol % of the ground corn product has a particle size of 60 μm or less, as measured according to ISO 13320:2009.

105. The ground corn product or process according to any one of paragraphs 87 to 104, wherein greater than 55 vol % of the ground corn product has a particle size of 400 μm or less, as measured according to ISO 13320:2009.

106. The ground corn product or process according to any one of paragraphs 87 to 105, wherein: the ground corn product has a $d_{10}$ by volume percent of 5 μm to 50 μm, a $d_{25}$ by volume percent of 30 μm to 150 μm, and a $d_{50}$ by volume percent of 120 μm to 350 μm, greater than 15 vol % of the ground corn product has a particle size of 60 μm or less, as measured according to ISO 13320:2009, and greater than 55 vol % of the ground corn product has a particle size of 400 μm or less, as measured according to ISO 13320:2009.

107. The process according to any one of paragraphs 93 to 106, wherein: a set of grinding teeth is disposed on the first rotatable disk, the second rotatable disk, or the stationary surface.

108. The process according to any one of paragraphs 93 to 106, wherein a first set of grinding teeth is disposed on the first rotatable disk, and wherein a second set of grinding teeth is disposed on either the second rotatable disk or the stationary surface.

109. The process according to any one of paragraphs 93 to 108, wherein the ground corn product passes through the shearing gap to exit the mill.

110. The process according to any one of paragraphs 93 to 109, wherein each set of grinding teeth comprises triangular teeth or rectangular teeth.

111. The ground corn product or process according to any one of paragraphs 87 to 110, wherein greater than 15 vol %, greater than 18 vol %, greater than 20 vol %, or greater than 25 vol % of the ground corn product has a particle size of 60 μm or less, as measured according to ISO 13320:2009.

112. The ground corn product or process according to any one of paragraphs 87 to 111, wherein greater than 40 vol %, greater than 50 vol %, greater than 55 vol %, greater than 60 vol %, or greater than 70 vol % of the ground corn product has a particle size of 400 μm or less, as measured according to ISO 13320:2009.

113. The ground corn product or process according to any one of paragraphs 87 to 112, wherein greater than 80 vol %, greater than 85 vol %, greater than 90 vol %, or greater than 95 vol % of the ground corn product has a particle size of 800 μm or less, as measured according to ISO 13320:2009.

114. The ground corn product or process according to any one of paragraphs 87 to 93 and 95 to 113, further comprising separating corn oil from the stillage, wherein the corn oil separated from the stillage is greater than 0.6 wt % of a total weight of the ground corn product.

115. The ground corn product or process according to any one of paragraphs 87 to 93 and 95 to 113, further comprising separating corn oil from the stillage, wherein the corn oil separated from the stillage is at least 0.7 wt % of a total weight of the ground corn product.

116. The ground corn product or process according to any one of paragraphs 87 to 93 and 95 to 113, further comprising separating corn oil from the stillage, wherein the corn oil separated from the stillage is at least 0.8 wt % of a total weight of the ground corn product.

117. The ground corn product or process according to any one of paragraphs 87 to 93 and 95 to 113, further comprising separating corn oil from the stillage, wherein the corn oil separated from the stillage is at least 0.9 wt % of a total weight of the ground corn product.

118. The ground corn product or process according to any one of paragraphs 87 to 93 and 95 to 113, further comprising separating corn oil from the stillage, wherein the corn oil separated from the stillage is at least 0.95 wt % of a total weight of the ground corn product.

Certain embodiments and features have been described using a set of numerical upper limits and a set of numerical lower limits. It should be appreciated that ranges including the combination of any two values, e.g., the combination of any lower value with any upper value, the combination of any two lower values, and/or the combination of any two upper values are contemplated unless otherwise indicated. Certain lower limits, upper limits and ranges appear in one or more claims below. All numerical values are "about" or "approximately" the indicated value, and take into account experimental error and variations that would be expected by a person having ordinary skill in the art.

Various terms have been defined above. To the extent a term used in a claim is not defined above, it should be given the broadest definition persons in the pertinent art have given that term as reflected in at least one printed publication or issued patent. And if applicable, all patents, test procedures, and other documents cited in this application are fully incorporated by reference to the extent such disclosure is not inconsistent with this application and for all jurisdictions in which such incorporation is permitted.

While the foregoing is directed to certain illustrative embodiments, other and further embodiments of the invention can be devised without departing from the basic scope thereof, and the scope thereof is determined by the claims that follow.

What is claimed is:

1. A process for making ethanol, comprising:
introducing a plurality of corn pieces into a mill, wherein the plurality of corn pieces comprises whole corn kernels, fragmented corn kernels, size-reduced corn kernels, milled corn kernels, or any mixture thereof;
milling the corn pieces in the mill to produce a ground corn product, wherein greater than 25 wt % of the ground corn product has a particle size of greater than 105 μm, and wherein greater than 80 wt % of the ground corn product has a particle size of 425 μm or less, as measured according to AOAC 965.22-1966;
processing the ground corn product to produce a fermentation mash comprising ethanol; and
separating at least a portion of the ethanol from the fermentation mash to produce a stillage.

2. The process of claim 1, further comprising separating corn oil from the stillage.

3. The process of claim 1, wherein the ground corn product has a $d_{50}$ by volume percent of 100 μm to 400 μm, as measured according to ISO 13320:2009.

4. The process of claim 1, wherein the mill is an air swept pulverizer or a disk mill fiberizer, and wherein the mill shears the corn pieces during milling to produce the ground corn product.

5. The process of claim 1, wherein:
greater than 85 wt % of the ground corn product has a particle size of 425 μm or less, as measured according to AOAC 965.22-1966,
greater than 15 vol % of the ground corn product has a particle size of 60 μm or less, as measured according to ISO 13320:2009, and
greater than 50 vol % of the ground corn product has a particle size of 400 μm or less, as measured according to ISO 13320:2009.

6. The process of claim 1, wherein:
the mill is an air swept pulverizer or a disk mill fiberizer, greater than 85 wt % of the ground corn product has a particle size of 425 μm or less, as measured according to AOAC 965.22-1966,
the ground corn product has a $d_{50}$ by volume percent of 100 μm to 400 μm, as measured according to ISO 13320:2009, the ground corn product has a crystallinity of greater than 75%, as compared to a crystallinity of the plurality of corn pieces prior to milling,
greater than 15 vol % of the ground corn product has a particle size of 60 μm or less, as measured according to ISO 13320:2009, and
greater than 50 vol % of the ground corn product has a particle size of 400 μm or less, as measured according to ISO 13320:2009.

7. The process of claim 1, further comprising separating corn oil from the stillage, wherein the mill comprises a first rotatable disk and either a second rotatable disk or a stationary surface, and wherein a distance separating the first rotatable disk and either the second rotatable disk or the stationary surface provides a shearing gap therebetween.

8. The process of claim 7, wherein milling the corn pieces in the mill comprises shearing the corn pieces between the first rotatable disk and either the second rotatable disk or the stationary surface in the shearing gap.

9. The process of claim 1, wherein greater than 30 wt % of the ground corn product has a particle size of 105 μm or less, as measured according to AOAC 965.22-1966.

10. The process of claim 1, wherein greater than 40 wt % of the ground corn product has a particle size of 150 μm or less, as measured according to AOAC 965.22-1966.

11. The process of claim 1, wherein greater than 50 wt % of the ground corn product has a particle size of 180 μm or less, as measured according to AOAC 965.22-1966.

12. The process of claim 1, wherein greater than 40 wt % of the ground corn product has a particle size of 105 μm or less, greater than 50 wt % of the ground corn product has a particle size of 150 μm or less, and wherein greater than 60 wt % of the ground corn product has a particle size of 180 μm or less, as measured according to AOAC 965.22-1966.

13. The process of claim 1, wherein milling the corn pieces in the mill to produce a ground corn product comprises shearing the corn pieces.

* * * * *